United States Patent
Brokx et al.

(10) Patent No.: US 12,286,476 B2
(45) Date of Patent: Apr. 29, 2025

(54) FCMR-BINDING MOLECULES AND USES THEREOF

(71) Applicant: UNIVERSITY HEALTH NETWORK, Toronto (CA)

(72) Inventors: Richard Brokx, Toronto (CA); Jacqueline M. Mason, Toronto (CA); Mark R. Bray, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 881 days.

(21) Appl. No.: 17/430,311

(22) PCT Filed: Feb. 14, 2020

(86) PCT No.: PCT/CA2020/050195
§ 371 (c)(1),
(2) Date: Aug. 11, 2021

(87) PCT Pub. No.: WO2020/163962
PCT Pub. Date: Aug. 20, 2020

(65) Prior Publication Data
US 2022/0089725 A1    Mar. 24, 2022

Related U.S. Application Data

(60) Provisional application No. 62/806,237, filed on Feb. 15, 2019.

(51) Int. Cl.
*C07K 16/28* (2006.01)
*A61P 35/02* (2006.01)
*C12N 15/63* (2006.01)

(52) U.S. Cl.
CPC .......... *C07K 16/2803* (2013.01); *A61P 35/02* (2018.01); *C12N 15/63* (2013.01); *C07K 2317/73* (2013.01); *C07K 2317/74* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,821,337 A | 10/1998 | Carter et al. |
| 5,859,205 A | 1/1999 | Adair et al. |
| 6,054,297 A | 4/2000 | Carter et al. |
| 6,180,370 B1 | 1/2001 | Queen et al. |
| 6,407,213 B1 | 6/2002 | Carter et al. |
| 7,657,380 B2 | 2/2010 | Lazar et al. |
| 10,023,648 B2 | 7/2018 | Hombach et al. |
| 2014/0271629 A1* | 9/2014 | Corbit .............. A61P 3/04 424/139.1 |
| 2016/0244525 A1 | 8/2016 | Yin et al. |
| 2016/0347854 A1 | 12/2016 | Hombach et al. |

FOREIGN PATENT DOCUMENTS

| | | |
|---|---|---|
| WO | WO 92/11018 A1 | 7/1992 |
| WO | WO 2013/136193 A2 | 9/2013 |
| WO | WO 2015/000059 A1 | 1/2015 |
| WO | WO 2016/127247 A1 | 8/2016 |
| WO | WO 2018/119425 A2 | 6/2018 |
| WO | WO 2020/163962 A1 | 8/2020 |

OTHER PUBLICATIONS

Baca, Manuel et al., "Antibody Humanization Using Monovalent Phage Display," J. Biol. Chem., Apr. 18, 1997, 272(16):10678-10684.
Baeuerle, Patrick A. et al., "NF-κB: Ten Years After," Cell, Oct. 4, 1996, 87:13-20.
Baldwin, Albert S., Jr. et al., "The NF-κB and IκB Proteins: New Discoveries and Insights," Ann. Rev. Immunol., 1996, 12:141.
Carter, Paul et al., "Humanization of an anti-p185HER2 antibody for human cancer therapy," Proc. Natl. Acad. Sci. USA, May 1992, 89:4285-4289.
Dayhoff, Margaret O., "Atlas of Protein Sequence and Structure," National Biomedical Research Foundation, 1978, 5(3):353-358.
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 2002, 169:3076-3084.
Edelman, Gerald M. et al., "The Covalent Structure of an Entire γG Immunoglobulin Molecule," Proc. Natl. Acad. Sci. USA, Mar. 21, 1969, 63:78-85.
Gorman, Scott D. et al., "Reshaping a therapeutic CD4 antibody," Proc. Natl. Acad. Sci. USA, May 1991, 88:4181-4185.
Gribskov, Michael et al., "Sigma factors from *E. coli, B. subtilis*, phage SP01, and phage T4 are homologous proteins," Nucl. Acids Res., 1986, 14(6):6745-6763.
He, Xing-Yue et al., "Humanization and Pharmacokinetics of a Monoclonal Antibody with Specificity for Both E- and P-Selectin," J. Immunol., 1998, 160: 1029-1035.
International Search Report and Written Opinion mailed Apr. 24, 2020 in International Application No. PCT/CA20/50195.
Jefferis, Roy et al., "Interaction sites on human IgG-Fc for FcgR: current models," Immunol. Lett., 2002, 82:57-65.
Jones, Peter T. et al., "Replacing the complementarity-determining regions in a human antibody with those from a mouse," Nature, May 29, 1986, 321:522-525.

(Continued)

*Primary Examiner* — Daniel E Kolker
*Assistant Examiner* — Maureen Varina Driscoll
(74) *Attorney, Agent, or Firm* — Morgan, Lewis & Bockius LLP

(57) ABSTRACT

The invention provides novel anti-FCMR antibodies, pharmaceutical compositions comprising such antibodies, and therapeutic methods of using such antibodies and pharmaceutical compositions for the treatment of diseases such as cancer or autoimmune disease.

33 Claims, 6 Drawing Sheets
Specification includes a Sequence Listing.

(56) References Cited

OTHER PUBLICATIONS

Krauss, Jürgen et al., "Specificity grafting of human antibody frameworks selected from a phage display library: generation of a highly stable humanized anti-CD22 single-chain Fv fragment," Protein Engineering, 2003, 16(10):753-759.
Langer, Robert, "New Methods of Drug Delivery," Sep. 28, 1990, Science, 249:1527-1533.
O'Connor, Shane J. et al., "Humanization of an antibody against human protein C and calcium-dependence involving framework residues," Protein Engineering, 1998, 11(4):321-328.
Presta, Leonard G. et al., "Humanization of an Anti-Vascular Endothelial Growth Factor Monoclonal Antibody for the Therapy of Solid Tumors and Other Disorders," Cancer Res., Oct. 15, 1997, 57(20):4593-4599.
Queen, Cary et al., "A humanized antibody that binds to the interleukin 2 receptor," Dec. 1989, Proc. Natl. Acad. Sci, USA, 86:10029-10033.
Rader, Christoph et al., "A phage display approach for rapid antibody humanization: Designed combinatorial V gene libraries," Proc. Natl. Acad. Sci. USA, Jul. 1998, 95: 8910-8915.
Riechmann, Lutz et al., "Reshaping human antibodies for therapy," Nature, Mar. 24, 1988, 332:323-327.
Roguska, Michael A. et al., "Humanization of murine monoclonal antibodies through variable domain resurfacing," Proc. Natl. Acad. Sci. USA, Feb. 1994, 91:969-973.
Roque, A. Cecilia A. et al., "Antibodies and Genetically Engineered Related Molecules: Production and Purification," 2004, Biotechnol. Prog., 20:639-654.
Rosok, Mae Joanne et al., "A Combinatorial Library Strategy for the Rapid Humanization of Anticarcinoma BR96 Fab," J. Biol. Chem, Sep. 13, 1996, 271(37): 22611-22618.
Schmitz, Gerd et al., "Pharmacogenomics: implications for laboratory medicine," Clinica Chimica Acta, 2001, 308:43-53.
Smith, Temple F. et al., "Comparison of Biosequences," Advances in Applied Mathematics, 1981, 2:482-489.
Steimer, Werner et al., "Pharmacogenetics: a new diagnostic tool in the management of antidepressive drug therapy," Clinica Chimica Acta, 2001, 308: 33-41.
Tan, Philip et al., "'Superhumanized' Antibodies: Reduction of Immunogenic Potential by Complementarity-Determining Region Grafting with Human Germline Sequences: Application to an Anti-CD28," J. Immunol., 2002, 169:1119-1125.
Tsurushita, Naoya, et al., "Humanization of Monoclonal Antibodies," Molecular Biology of B Cells, Elsevier Science (USA), 2004, 533-545.
Verhoeyen, Martine et al., "Reshaping Human Antibodies: Grafting an Antilysozyme Activity," Science, Mar. 25, 1988, 239:1534-1536.
Wu, Herren et al., "Humanization of a Murine Monoclonal Antibody by Simultaneous Optimization of Framework and CDR Residues," 1999, J. Mol. Biol. 294:151-162.
Ye, Jian et al., "IgBLAST: an immunoglobulin variable domain sequence analysis tool," Nucleic Acids Research, 2013, 41:W34-W40.
Pallasch, C. et al., "Overexpression of TOSO in CLL is triggered by B-cell receptor signaling and associated with progressive disease," Blood, Nov. 15, 2008, 112(10):4213-4219.
Tan, Y. et al., "Anti-TOSO antibody treatment promotes T cell activation-induced cell death (AICD) in vitro and in vivo," Chin. Sci. Bull., Immunology, Science China Press, 2014, 59(13):1374-1385.
Kubagawa, Y. et al., "Monoclonal Antibodies Specific for Human IgM Fc Receptor Inhibit Ligand-binding Activity," Monoclonal Antibodies in Immunodiagnosis and Immunotherapy, 2014, 33(6):393-400.
Nguyen, X. et al., "Toso regulates the balance between apoptotic and nonapoptotic death receptor signaling by facilitating RIP1 ubiquitination," Immunobiology, Blood, Jul. 21, 2011, 118(3):598-608.
Yi, T. et al., "Anti-TOSO antibody treatment promotes T cell activation-induced cell death (AICD) in vitro and in vivo," Chinese Science Bulletin, 2014, 59:1374-1385.
First Office Action for corresponding Chinese Patent Application No. 202080025378, dated Jun. 27, 2024, 13 pages, English translation.
EPC Rule 94(3) Communication for corresponding European Patent Application No. 20756467.5, dated Aug. 19, 2024, 5 pages.

\* cited by examiner

FIGURE 6

| Antibody | $k_a$ (1/Ms) | $k_d$ (1/s) | $K_D$ (M) |
|---|---|---|---|
| 2A5 | 3.47x10$^4$ | 2.47x10$^{-4}$ | 7.21x10$^{-9}$ |
| 2H2 | 3.45x10$^4$ | 8.87x10$^{-4}$ | 2.57x10$^{-8}$ |

```
                        SEQUENCE LISTING

<160> NUMBER OF SEQ ID NOS: 48

<210> SEQ ID NO 1
<211> LENGTH: 145
<212> TYPE: PRT
<213> ORGANISM: Artificial Sequence
<220> FEATURE:
<223> OTHER INFORMATION: FCMR Heavy chain variable region (IgG2b)

<400> SEQUENCE: 1

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Asn Ser Gly Gly Ser Ser Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Asn Tyr Asp Ser Ser Tyr Arg Tyr Ala Met
        115                 120                 125

Asp Tyr Trp Gly Gln Gly Thr Ser Val Thr Val Ser Ser Ala Lys Thr
    130                 135                 140

Thr
145

<210> SEQ ID NO 2
<211> LENGTH: 131
<212> TYPE: PRT
<213> ORGANISM: Artificial Sequence
<220> FEATURE:
<223> OTHER INFORMATION: FCMR Light chain variable region (IgG2b)

<400> SEQUENCE: 2

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30
```

```
Ala Ser Leu Gly Glu Arg Val Thr Ile Thr Cys Lys Ala Ser Gln Asp
        35                  40                  45

Ile Asn Asn Phe Leu Ser Trp Phe Gln Gln Lys Pro Gly Lys Ser Pro
 50                  55                  60

Lys Thr Leu Ile Tyr Arg Ala Asn Gly Leu Val Asp Gly Val Pro Ser
 65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Ile Tyr Tyr Cys Leu Gln Tyr Asp
                100                 105                 110

Glu Phe Pro Pro Thr Phe Gly Gly Gly Thr Lys Leu Glu Phe Lys Arg
        115                 120                 125

Ala Asp Ala
    130
```

<210> SEQ ID NO 3
<211> LENGTH: 290
<212> TYPE: PRT
<213> ORGANISM: Artificial Sequence
<220> FEATURE:
<223> OTHER INFORMATION: FCMR Heavy chain variable region (IgG1)

<400> SEQUENCE: 3

```
Met Asn Phe Gly Leu Ser Leu Ile Phe Leu Ala Leu Ile Leu Lys Gly
 1               5                  10                  15

Val Gln Cys Glu Val Gln Leu Val Glu Ser Gly Gly Asp Leu Val Lys
            20                  25                  30

Pro Gly Gly Ser Leu Lys Pro Ser Cys Ala Ala Ser Gly Phe Ser Phe
        35                  40                  45

Ser Ser Tyr Gly Met Ser Trp Val Arg Gln Thr Pro Asp Lys Arg Leu
 50                  55                  60

Glu Trp Val Ala Thr Ile Ser Ser Gly Gly Ser Asn Ile Gln Tyr Leu
 65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
                100                 105                 110

Tyr Tyr Cys Val Arg His Asp Asp Gly Ser Ser Tyr Gln Tyr Ala Met
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
                180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Gln Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255
```

```
Ser Val Phe Ile Phe Pro Pro Lys Pro Lys Asp Val Leu Thr Ile Thr
            260                 265                 270

Leu Thr Pro Lys Val Thr Cys Val Val Asp Ile Ser Lys Asp Asp
        275                 280                 285

Gln Gly
    290

<210> SEQ ID NO 4
<211> LENGTH: 226
<212> TYPE: PRT
<213> ORGANISM: Artificial Sequence
<220> FEATURE:
<223> OTHER INFORMATION: FCMR Light chain variable region (IgG1)

<400> SEQUENCE: 4

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Asn Ser Tyr Leu Ser Trp Phe Gln Gln Lys Pro Gly Lys
    50                  55                  60

Ser Pro Lys Thr Leu Ile Tyr Arg Ala Asn Arg Leu Val Asp Gly Val
65                  70                  75                  80

Pro Ser Arg Phe Ser Gly Ser Gly Ser Gly Gln Asp Leu Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Leu Thr Phe Gly Ala Gly Thr Lys Leu Glu Leu
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Arg Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro
225

<210> SEQ ID NO 5
<211> LENGTH: 279
<212> TYPE: PRT
<213> ORGANISM: Artificial Sequence
<220> FEATURE:
<223> OTHER INFORMATION: FCMR Heavy chain variable region (IgG1)

<400> SEQUENCE: 5

Met Asn Phe Gly Leu Ser Leu Ile Phe Leu Ala Leu Ile Leu Lys Gly
1               5                   10                  15
```

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Thr Tyr Asn Ser Tyr Leu
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Thr Ala Met
            100                 105                 110

Tyr Tyr Cys Ala Arg His Asp Asp Gly Ser Arg Tyr Gln Tyr Ile Val
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Gln Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys
        275

<210> SEQ ID NO 6
<211> LENGTH: 235
<212> TYPE: PRT
<213> ORGANISM: Artificial Sequence
<220> FEATURE:
<223> OTHER INFORMATION: FCMR Light chain variable region (IgG1)

<400> SEQUENCE: 6

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Asn Ser Tyr Leu Ser Trp Phe Gln Lys Pro Gly Lys
    50                  55                  60

Ser Pro Lys Thr Leu Ile Tyr Arg Ala Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Leu Thr Phe Gly Ala Gly Thr Lys Leu Glu Leu
            115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Arg Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
                195                 200                 205

Glu Arg His Asn Ser Tyr Thr Cys Glu Ala Thr His Lys Thr Ser Thr
            210                 215                 220

Ser Pro Val Val Asp Ile Ser Lys Asp Asp Gln
225                 230                 235

<210> SEQ ID NO 7
<211> LENGTH: 281
<212> TYPE: PRT
<213> ORGANISM: Artificial Sequence
<220> FEATURE:
<223> OTHER INFORMATION: FCMR Heavy chain variable region (IgG1)

<400> SEQUENCE: 7

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Tyr Ile Asn Trp Val Lys Gln Ser His Gly Lys Ser Leu
50                  55                  60

Glu Trp Ile Gly Asp Val Tyr Pro Asn Asn Gly Gly Thr Ser Tyr Asn
65                  70                  75                  80

Gln Lys Phe Lys Asp Lys Ala Thr Leu Thr Val Asp Lys Ser Ser Asn
                85                  90                  95

Thr Ala Tyr Met Glu Leu Arg Ser Leu Thr Ser Ala Asp Ser Ala Val
            100                 105                 110

Tyr Tyr Cys Ala Arg Gln Leu Thr Tyr Trp Gly Arg Gly Thr Leu Val
        115                 120                 125

Thr Val Ser Ala Ala Lys Thr Thr Pro Pro Ser Val Tyr Pro Leu Ala
130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Gln Thr Val Thr Cys Asn Val Ala His Pro Ala Ser Ser Thr Lys
210                 215                 220

```
Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
            245                 250                 255

Lys Asp Val Leu Thr Ile Thr Leu Thr Pro Lys Val Thr Cys Val Val
            260                 265                 270

Val Asp Ile Ser Lys Asp Asp Gln Gly
        275                 280

<210> SEQ ID NO 8
<211> LENGTH: 230
<212> TYPE: PRT
<213> ORGANISM: Artificial Sequence
<220> FEATURE:
<223> OTHER INFORMATION: FCMR Light chain variable region (IgG1)

<400> SEQUENCE: 8

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Ser
            20                  25                  30

Val Ser Ala Gly Glu Lys Val Thr Met Ser Cys Lys Ala Ser Gln Ser
        35                  40                  45

Leu Leu Lys Ser Gly Lys Gln Glu Asn Tyr Leu Ala Trp Tyr Gln Gln
    50                  55                  60

Lys Pro Gly Leu Pro Pro Lys Val Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp His Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Arg Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro
225                 230

<210> SEQ ID NO 9
<211> LENGTH: 282
<212> TYPE: PRT
<213> ORGANISM: Artificial Sequence
<220> FEATURE:
<223> OTHER INFORMATION: FCMR Heavy chain variable region (IgG1)
```

```
<400> SEQUENCE: 9

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ser Ser Val Lys Leu Ser Cys Lys Ala Ser Gly Tyr Thr Phe
        35                  40                  45

Thr Asn His Trp Leu His Trp Val Lys Gln Arg Pro Ile Gln Gly Leu
    50                  55                  60

Glu Trp Ile Gly Tyr Ile Asp Pro Ser Asp Ser Leu Thr His Tyr Asn
65                  70                  75                  80

Gln Asn Phe Lys Asp Lys Ala Thr Leu Thr Val Asp Lys Ser Ser Ser
            85                  90                  95

Thr Ala Tyr Met Gln Leu Ser Ser Leu Thr Ser Glu Asp Ser Ala Val
        100                 105                 110

Tyr Tyr Cys Ala Arg Phe Ser Phe Ala Tyr Trp Gly Gln Gly Thr Leu
    115                 120                 125

Val Thr Val Ser Ala Ala Lys Thr Thr Pro Pro Ser Val Tyr Pro Leu
130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Pro Ser Ser Thr Trp
        195                 200                 205

Pro Ser Gln Thr Val Thr Cys Asn Val Ala His Pro Ala Ser Ser Thr
    210                 215                 220

Lys Val Asp Lys Lys Ile Val Pro Arg Asp Cys Gly Cys Lys Pro Cys
225                 230                 235                 240

Ile Cys Thr Val Pro Glu Val Ser Ser Val Phe Ile Phe Pro Pro Lys
                245                 250                 255

Pro Lys Asp Val Leu Thr Ile Thr Leu Thr Pro Lys Val Thr Cys Val
            260                 265                 270

Val Val Asp Ile Ser Lys Asp Gln Gly
        275                 280

<210> SEQ ID NO 10
<211> LENGTH: 228
<212> TYPE: PRT
<213> ORGANISM: Artificial Sequence
<220> FEATURE:
<223> OTHER INFORMATION: FCMR Light chain variable region (IgG1)

<400> SEQUENCE: 10

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60
```

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
            85                  90                  95

Thr Leu Lys Ile Ser Arg Val Glu Ala Glu Asp Leu Gly Val Tyr Tyr
                100                 105                 110

Cys Trp Gln Gly Thr His Leu Trp Thr Phe Gly Gly Gly Thr Lys Leu
            115                 120                 125

Glu Ile Lys Arg Ala Asp Ala Ala Pro Thr Val Ser Ile Phe Pro Pro
            130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
210                 215                 220

Ser Thr Ser Pro
225

<210> SEQ ID NO 11
<211> LENGTH: 293
<212> TYPE: PRT
<213> ORGANISM: Artificial Sequence
<220> FEATURE:
<223> OTHER INFORMATION: FCMR Heavy chain variable region (IgG2b)

<400> SEQUENCE: 11

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Tyr Ile Asn Trp Val Lys Gln Ser His Gly Lys Ser Leu
    50                  55                  60

Glu Trp Ile Gly Asp Ile Tyr Pro Asn Asn Gly Gly Thr Asn Tyr Asn
65                  70                  75                  80

Gln Lys Phe Lys Gly Lys Ala Thr Leu Thr Val Asp Lys Ser Ser Ser
            85                  90                  95

Thr Ala Tyr Met Glu Leu Arg Ser Leu Thr Ser Glu Asp Ser Ala Val
                100                 105                 110

Tyr Tyr Cys Ala Arg Gln Leu Thr Tyr Trp Gly Pro Gly Thr Leu Val
            115                 120                 125

Thr Val Ser Ala Ala Lys Thr Thr Pro Pro Ser Val Tyr Pro Leu Ala
            130                 135                 140

Pro Gly Cys Gly Asp Thr Thr Gly Ser Ser Val Thr Leu Gly Cys Leu
145                 150                 155                 160

Val Lys Gly Tyr Phe Pro Glu Ser Val Thr Val Thr Trp Asn Ser Gly
                165                 170                 175

Ser Leu Ser Ser Val His Thr Phe Pro Ala Leu Leu Gln Ser Gly
            180                 185                 190

```
Leu Tyr Thr Met Ser Ser Ser Val Thr Val Pro Ser Ser Thr Trp Pro
            195                 200                 205

Ser Gln Thr Val Thr Cys Ser Val Ala His Pro Ala Ser Ser Thr Thr
    210                 215                 220

Val Asp Lys Lys Leu Glu Pro Ser Gly Pro Ile Ser Thr Ile Asn Pro
225                 230                 235                 240

Cys Pro Pro Cys Lys Glu Cys His Lys Cys Pro Ala Pro Asn Leu Glu
                245                 250                 255

Gly Gly Pro Ser Val Phe Ile Phe Pro Pro Asn Ile Lys Asp Val Leu
                260                 265                 270

Met Ile Ser Leu Thr Pro Lys Val Thr Cys Val Val Val Asp Val Ser
            275                 280                 285

Glu Asp Asp Gln Gly
        290
```

```
<210> SEQ ID NO 12
<211> LENGTH: 230
<212> TYPE: PRT
<213> ORGANISM: Artificial Sequence
<220> FEATURE:
<223> OTHER INFORMATION: FCMR Light chain variable region (IgG2b)

<400> SEQUENCE: 12

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Ser
            20                  25                  30

Val Ser Val Gly Glu Lys Val Thr Met Asn Cys Lys Ser Ser Gln Ser
        35                  40                  45

Leu Leu Asn Ser Gly His Gln Glu Asn Tyr Leu Ala Trp Tyr Gln Gln
    50                  55                  60

Lys Pro Gly Gln Pro Pro Lys Val Leu Ile Tyr Gly Ala Val Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp His Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Arg Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro
225                 230
```

```
<210> SEQ ID NO 13
<211> LENGTH: 8
```

```
<212> TYPE: PRT
<213> ORGANISM: Artificial Sequence
<220> FEATURE:
<223> OTHER INFORMATION: FCMR Heavy chain variable region CDR1 (IgG2b)

<400> SEQUENCE: 13

Gly Phe Thr Phe Ser Ser Tyr Gly
1               5

<210> SEQ ID NO 14
<211> LENGTH: 8
<212> TYPE: PRT
<213> ORGANISM: Artificial Sequence
<220> FEATURE:
<223> OTHER INFORMATION: FCMR Heavy chain variable region CDR2 (IgG2b)

<400> SEQUENCE: 14

Ile Asn Ser Gly Gly Ser Ser Ile
1               5

<210> SEQ ID NO 15
<211> LENGTH: 15
<212> TYPE: PRT
<213> ORGANISM: Artificial Sequence
<220> FEATURE:
<223> OTHER INFORMATION: FCMR Heavy chain variable region CDR3 (IgG2b)

<400> SEQUENCE: 15

Ala Arg His Asn Tyr Asp Ser Ser Tyr Arg Tyr Ala Met Asp Tyr
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: FCMR Light chain variable region CDR1 (IgG2b)

<400> SEQUENCE: 16

Gln Asp Ile Asn Asn Phe
1               5

<210> SEQ ID NO 17

<400> SEQUENCE: 17

000

<210> SEQ ID NO 18
<211> LENGTH: 9
<212> TYPE: PRT
<213> ORGANISM: Artificial Sequence
<220> FEATURE:
<223> OTHER INFORMATION: FCMR Light chain variable region CDR3 (IgG2b)

<400> SEQUENCE: 18

Leu Gln Tyr Asp Glu Phe Pro Pro Thr
1               5

<210> SEQ ID NO 19
<211> LENGTH: 8
<212> TYPE: PRT
<213> ORGANISM: Artificial Sequence
<220> FEATURE:
<223> OTHER INFORMATION: FCMR Heavy chain variable region CDR1 (IgG1)
```

```
<400> SEQUENCE: 19

Gly Phe Ser Phe Ser Ser Tyr Gly
1               5

<210> SEQ ID NO 20
<211> LENGTH: 7
<212> TYPE: PRT
<213> ORGANISM: Artificial Sequence
<220> FEATURE:
<223> OTHER INFORMATION: FCMR Heavy chain variable region CDR2 (IgG1)

<400> SEQUENCE: 20

Ser Ser Gly Gly Ser Asn Ile
1               5

<210> SEQ ID NO 21
<211> LENGTH: 15
<212> TYPE: PRT
<213> ORGANISM: Artificial Sequence
<220> FEATURE:
<223> OTHER INFORMATION: FCMR Heavy chain variable region CDR3 (IgG1)

<400> SEQUENCE: 21

Val Arg His Asp Asp Gly Ser Ser Tyr Gln Tyr Ala Met Asp Tyr
1               5                   10                  15

<210> SEQ ID NO 22
<211> LENGTH: 6
<212> TYPE: PRT
<213> ORGANISM: Artificial Sequence
<220> FEATURE:
<223> OTHER INFORMATION: FCMR Light chain variable region CDR1 (IgG1)

<400> SEQUENCE: 22

Gln Asp Ile Asn Ser Tyr
1               5

<210> SEQ ID NO 23

<400> SEQUENCE: 23

000

<210> SEQ ID NO 24
<211> LENGTH: 9
<212> TYPE: PRT
<213> ORGANISM: Artificial Sequence
<220> FEATURE:
<223> OTHER INFORMATION: FCMR Light chain variable region CDR3 (IgG1)

<400> SEQUENCE: 24

Leu Gln Tyr Asp Glu Phe Pro Leu Thr
1               5

<210> SEQ ID NO 25
<211> LENGTH: 8
<212> TYPE: PRT
<213> ORGANISM: Artificial Sequence
<220> FEATURE:
<223> OTHER INFORMATION: FCMR Heavy chain variable region CDR1 (IgG1)

<400> SEQUENCE: 25

Gly Phe Thr Phe Ser Ser Tyr Gly
1               5
```

```
<210> SEQ ID NO 26
<211> LENGTH: 8
<212> TYPE: PRT
<213> ORGANISM: Artificial Sequence
<220> FEATURE:
<223> OTHER INFORMATION: FCMR Heavy chain variable region CDR2 (IgG1)

<400> SEQUENCE: 26

Ile Ser Ser Gly Gly Thr Tyr Asn
1               5

<210> SEQ ID NO 27
<211> LENGTH: 15
<212> TYPE: PRT
<213> ORGANISM: Artificial Sequence
<220> FEATURE:
<223> OTHER INFORMATION: FCMR Heavy chain variable region CDR3 (IgG1)

<400> SEQUENCE: 27

Ala Arg His Asp Asp Gly Ser Arg Tyr Gln Tyr Ile Val Asp Tyr
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: FCMR Light chain variable region CDR1 (IgG1)

<400> SEQUENCE: 28

Gln Asp Ile Asn Ser Tyr
1               5

<210> SEQ ID NO 29

<400> SEQUENCE: 29

000

<210> SEQ ID NO 30
<211> LENGTH: 9
<212> TYPE: PRT
<213> ORGANISM: Artificial Sequence
<220> FEATURE:
<223> OTHER INFORMATION: FCMR Light chain variable region CDR3 (IgG1)

<400> SEQUENCE: 30

Leu Gln Tyr Asp Glu Phe Pro Leu Thr
1               5

<210> SEQ ID NO 31
<211> LENGTH: 8
<212> TYPE: PRT
<213> ORGANISM: Artificial Sequence
<220> FEATURE:
<223> OTHER INFORMATION: FCMR Heavy chain variable region CDR1 (IgG1)

<400> SEQUENCE: 31

Gly Tyr Thr Phe Thr Asp Tyr Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: FCMR Heavy chain variable region CDR2 (IgG1)
```

```
<400> SEQUENCE: 32

Val Tyr Pro Asn Asn Gly Gly Thr
1               5

<210> SEQ ID NO 33
<211> LENGTH: 6
<212> TYPE: PRT
<213> ORGANISM: Artificial Sequence
<220> FEATURE:
<223> OTHER INFORMATION: FCMR Heavy chain variable region CDR3 (IgG1)

<400> SEQUENCE: 33

Ala Arg Gln Leu Thr Tyr
1               5

<210> SEQ ID NO 34
<211> LENGTH: 12
<212> TYPE: PRT
<213> ORGANISM: Artificial Sequence
<220> FEATURE:
<223> OTHER INFORMATION: FCMR Light chain variable region CDR1 (IgG1)

<400> SEQUENCE: 34

Gln Ser Leu Leu Lys Ser Gly Lys Gln Glu Asn Tyr
1               5                   10

<210> SEQ ID NO 35

<400> SEQUENCE: 35

000

<210> SEQ ID NO 36
<211> LENGTH: 9
<212> TYPE: PRT
<213> ORGANISM: Artificial Sequence
<220> FEATURE:
<223> OTHER INFORMATION: FCMR Light chain variable region CDR3 (IgG1)

<400> SEQUENCE: 36

Gln Asn Asp His Ser Tyr Pro Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: FCMR Heavy chain variable region CDR1 (IgG1)

<400> SEQUENCE: 37

Gly Tyr Thr Phe Thr Asn His Trp
1               5

<210> SEQ ID NO 38
<211> LENGTH: 8
<212> TYPE: PRT
<213> ORGANISM: Artificial Sequence
<220> FEATURE:
<223> OTHER INFORMATION: FCMR Heavy chain variable region CDR2 (IgG1)

<400> SEQUENCE: 38

Ile Asp Pro Ser Asp Ser Leu Thr
1               5

<210> SEQ ID NO 39
```

```
<211> LENGTH: 7
<212> TYPE: PRT
<213> ORGANISM: Artificial Sequence
<220> FEATURE:
<223> OTHER INFORMATION: FCMR Heavy chain variable region CDR3 (IgG1)

<400> SEQUENCE: 39

Ala Arg Phe Ser Phe Ala Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: FCMR Light chain variable region CDR1 (IgG1)

<400> SEQUENCE: 40

Gln Ser Leu Leu Asp Ser Asp Gly Lys Thr Tyr
1               5                   10

<210> SEQ ID NO 41

<400> SEQUENCE: 41

000

<210> SEQ ID NO 42
<211> LENGTH: 9
<212> TYPE: PRT
<213> ORGANISM: Artificial Sequence
<220> FEATURE:
<223> OTHER INFORMATION: FCMR Light chain variable region CDR3 (IgG1)

<400> SEQUENCE: 42

Trp Gln Gly Thr His Leu Trp Thr Phe
1               5

<210> SEQ ID NO 43
<211> LENGTH: 8
<212> TYPE: PRT
<213> ORGANISM: Artificial Sequence
<220> FEATURE:
<223> OTHER INFORMATION: FCMR Heavy chain variable region CDR1 (IgG2b)

<400> SEQUENCE: 43

Gly Tyr Thr Phe Thr Asp Tyr Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: FCMR Heavy chain variable region CDR2 (IgG2b)

<400> SEQUENCE: 44

Ile Tyr Pro Asn Asn Gly Gly Thr
1               5

<210> SEQ ID NO 45
<211> LENGTH: 6
<212> TYPE: PRT
<213> ORGANISM: Artificial Sequence
<220> FEATURE:
<223> OTHER INFORMATION: FCMR Heavy chain variable region CDR3 (IgG2b)
```

```
<400> SEQUENCE: 45

Ala Arg Gln Leu Thr Tyr
1               5

<210> SEQ ID NO 46
<211> LENGTH: 12
<212> TYPE: PRT
<213> ORGANISM: Artificial Sequence
<220> FEATURE:
<223> OTHER INFORMATION: FCMR Light chain variable region CDR1 (IgG2b)

<400> SEQUENCE: 46

Gln Ser Leu Leu Asn Ser Gly His Gln Glu Asn Tyr
1               5                   10

<210> SEQ ID NO 47

<400> SEQUENCE: 47

000

<210> SEQ ID NO 48
<211> LENGTH: 9
<212> TYPE: PRT
<213> ORGANISM: Artificial Sequence
<220> FEATURE:
<223> OTHER INFORMATION: FCMR Light chain variable region CDR3 (IgG2b)

<400> SEQUENCE: 48

Gln Asn Asp His Ser Tyr Pro Leu Thr
1               5
```

FCMR-BINDING MOLECULES AND USES THEREOF

CROSS REFERENCE TO RELATED APPLICATION

The present application claims the benefit of priority to U.S. Provisional Application No. 62/806,237, filed Feb. 15, 2019, the contents of which is expressly incorporated herein in its entirety for all purposes.

TECHNICAL FIELD

The invention provides antibodies that specifically bind to FCMR, e.g., human FCMR (hFCMR), and pharmaceutical compositions comprising such FCMR-binding antibodies thereof. Methods of using the antibodies of the invention to detect human FCMR or to modulate human FCMR activity in the treatment of various diseases, including inflammatory diseases, autoimmune diseases and cancer, are also encompassed by the invention.

BACKGROUND OF THE INVENTION

Fc receptor for IgM FCMR, also called Toso or FAIM3 (Fas apoptosis inhibitory molecule 3)] is a type I transmembrane receptor that belongs to the immunoglobulin gene superfamily Natural mutations of FCMR in humans have not been identified. FCMR was initially implicated in the regulation of CD95 (Fas/Apo1)—and tumor necrosis factor receptor (TNFR)-dependent T cell apoptosis Subsequent studies identified FCMR as an Fc receptor for soluble IgM.

In humans, dysregulated expression of FCMR has been observed in patients with various B cell malignancies, and in particular in patients with chronic lymphocytic leukemia (CLL) FCMR-deficient mice are resistant to the development of experimental autoimmune encephalomyelitis (EAE), and exhibit reduced pathogenic T cell responses A later study showed that FCMR-deficient T cells fail to produce IL-17 following stimulation, which is a critical driving cytokine for EAE. FCMR is also reported to play a role during inflammatory responses to infection. Studies on FCMR-deficient mice have revealed a strong immunoprotective function of FCMR in a model of *Listeria* infection, and during lymphocytic choriomeningitis virus (LCMV) infection.

Collectively, these findings suggest that the development of agents useful in modulating signaling from FCMR would be of great benefit in diseases involving dysregulation of the immune system, including inflammatory diseases, autoimmune diseases and cancer.

SUMMARY OF THE INVENTION

In one aspect, the present invention relates to novel anti-FCMR antibodies. In some embodiments, the anti-FCMR antibodies include a heavy chain variable region comprising an amino acid sequence of SEQ ID NO:1 and a light chain variable region comprising an amino acid sequence of SEQ ID NO:2. In some embodiments, the anti-FCMR antibodies include a heavy chain variable region comprising an amino acid sequence of SEQ ID NO:3 and a light chain variable region comprising an amino acid sequence of SEQ ID NO:4. In some embodiments, the anti-FCMR antibodies include a heavy chain variable region comprising an amino acid sequence of SEQ ID NO:5 and a light chain variable region comprising an amino acid sequence of SEQ ID NO:6. In some embodiments, the anti-FCMR antibodies include a heavy chain variable region comprising an amino acid sequence of SEQ ID NO:7 and a light chain variable region comprising an amino acid sequence of SEQ ID NO:8. In some embodiments, the anti-FCMR antibodies include a heavy chain variable region comprising an amino acid sequence of SEQ ID NO:9 and a light chain variable region comprising an amino acid sequence of SEQ ID NO:10. In some embodiments, the anti-FCMR antibodies include a heavy chain variable region comprising an amino acid sequence of SEQ ID NO:11 and a light chain variable region comprising an amino acid sequence of SEQ ID NO:12.

In some embodiments, the anti-FCMR antibodies include a vhCDR1 comprising SEQ ID NO:13, a vhCDR2 comprising SEQ ID NO:14, a vhCDR3 comprising SEQ ID NO:15, a vlCDR1 comprising SEQ ID NO:16, a vlCDR2 comprising amino acid sequence RAN, and a vlCDR3 comprising SEQ ID NO:18. In some embodiments, the anti-FCMR antibodies include a vhCDR1 comprising SEQ ID NO:19, a vhCDR2 comprising SEQ ID NO:20, a vhCDR3 comprising SEQ ID NO:21, a vlCDR1 comprising SEQ ID NO:22, a vlCDR2 comprising amino acid sequence RAN, and a vlCDR3 comprising SEQ ID NO:24. In some embodiments, the anti-FCMR antibodies include a vhCDR1 comprising SEQ ID NO:25, a vhCDR2 comprising SEQ ID NO:26, a vhCDR3 comprising SEQ ID NO:27, a vlCDR1 comprising SEQ ID NO:28, a vlCDR2 comprising amino acid sequence RAN, and a vlCDR3 comprising SEQ ID NO:30. In some embodiments, the anti-FCMR antibodies include a vhCDR1 comprising SEQ ID NO:31, a vhCDR2 comprising SEQ ID NO:32, a vhCDR3 comprising SEQ ID NO:33, a vlCDR1 comprising SEQ ID NO:34, a vlCDR2 comprising amino acid sequence GAS, and a vlCDR3 comprising SEQ ID NO:36. In some embodiments, the anti-FCMR antibodies include a vhCDR1 comprising SEQ ID NO:37, a vhCDR2 comprising SEQ ID NO:38, a vhCDR3 comprising SEQ ID NO:39, a vlCDR1 comprising SEQ ID NO:40, a vlCDR2 comprising amino acid sequence LVS, and a vlCDR3 comprising SEQ ID NO:42. In some embodiments, the anti-FCMR antibodies include a vhCDR1 comprising SEQ ID NO:43, a vhCDR2 comprising SEQ ID NO:44, a vhCDR3 comprising SEQ ID NO:45, a vlCDR1 comprising SEQ ID NO:46, a vlCDR2 comprising amino acid sequence GAV, and a vlCDR3 comprising SEQ ID NO:48.

In some embodiments, the anti-FCMR antibodies described herein bind human FCMR.

In some embodiments, the anti-FCMR antibodies described herein include a constant region with an amino acid sequence at least 90% identical to a human IgG. In some embodiments, the IgG is selected from an IgG1, IgG2, IgG3 or IgG4. In some embodiments, the IgG is an IgG1. In some embodiments the IgG is an IgG2.

In another aspect, the present invention relates to a nucleic acid composition encoding any one of the anti-FCMR antibodies described herein.

Another aspect of the present invention relates to an expression vector composition that includes any one of the nucleic acid compositions described herein. In some embodiments, the first nucleic acid is contained in a first expression vector and the second nucleic acid is contained in a second expression vector. In some other embodiments, the first nucleic acid and the second nucleic acid are contained in a single expression vector.

Another aspect of the present invention relates to a host cell that includes any one of the expression vectors described herein. Also presented is a method of making anti-FCMR antibodies, and the method includes culturing the host cell under conditions wherein the antibodies expressed, and recovering the antibodies.

In another aspect, the present invention relates to a composition that includes any one of the anti-FCMR antibodies described herein, and a pharmaceutical acceptable carrier or diluent.

Also described is a method of modulating an immune response in a subject, and the method includes administering to the subject an effective amount of any one of the anti-FCMR antibodies described herein, or any one of the compositions described herein. In some embodiments, the method inhibits an immune response in the subject and the method includes administering to the subject an effective amount of an anti-FCMR antibody that serves as a FCMR antagonist, or a pharmaceutical composition thereof. In some embodiments, the method stimulates an immune response in the subject and the method includes administering to the subject an effective amount of an anti-FCMR antibody that serves as a FCMR agonist, or a pharmaceutical composition thereof.

In some embodiments, the method suppresses an immune response in the subject, and the method includes administering to the subject an effective amount of an anti-FCMR antibody.

In some embodiments, the method stimulates an immune response in the subject, and the method includes administering to the subject an effective amount of an anti-FCMR antibody.

In another aspect, the present invention relates to a method of treating cancer in a subject, and the method includes administering to the subject an effective amount of an anti-FCMR antibody described herein, or a composition thereof. In some embodiments, the cancer to be treated upregulates FCMR compared to the corresponding non-cancerous tissue. In some embodiments, the cancer to be treated can be a B cell malignancy. In some embodiments, the B cell malignancy is chronic lymphocytic leukemia. In some embodiments, an anti-FCMR antibody is used in combination with one or more additional anti-cancer therapeutic agents. In some embodiments, such anti-cancer therapeutic agents are other immune checkpoint inhibitors, such as a PD-1 inhibitor, a PD-L1 inhibitor, a CTLA-4 inhibitor, a TIM-3 inhibitor, and a LAG-3 inhibitor.

In another aspect, the present invention relates to a method of treating an autoimmune disease in a subject, and the method includes administering to the subject an effective amount of an anti-FCMR antibody described herein, or a composition thereof. In some embodiments, an anti-FCMR antibody is used in combination with one or more additional anti-inflammatory therapeutic agents.

In another aspect, the present invention relates to a method of treating a bacterial infection in a subject, and the method includes administering to the subject an effective amount of an anti-FCMR antibody described herein, or a composition thereof. In some embodiments, an anti-FCMR antibody is used in combination with one or more antibiotic therapeutic agents.

In another aspect, the present invention relates to a method of treating a viral infection in a subject, and the method includes administering to the subject an effective amount of an anti-FCMR antibody described herein, or a composition thereof. In some embodiments, an anti-FCMR antibody is used in combination with one or more additional anti-viral therapeutic agents.

BRIEF DESCRIPTION OF THE DRAWINGS

The invention may be best understood from the following detailed description when read in conjunction with the accompanying drawings. Included in the drawings are the following figures:

FIG. 6 shows affinity of FCMR antibodies 2A5 and 2H2 for FCMR-Fc protein determined by surface plasmon resonance.

DETAILED DESCRIPTION

Figure 1:
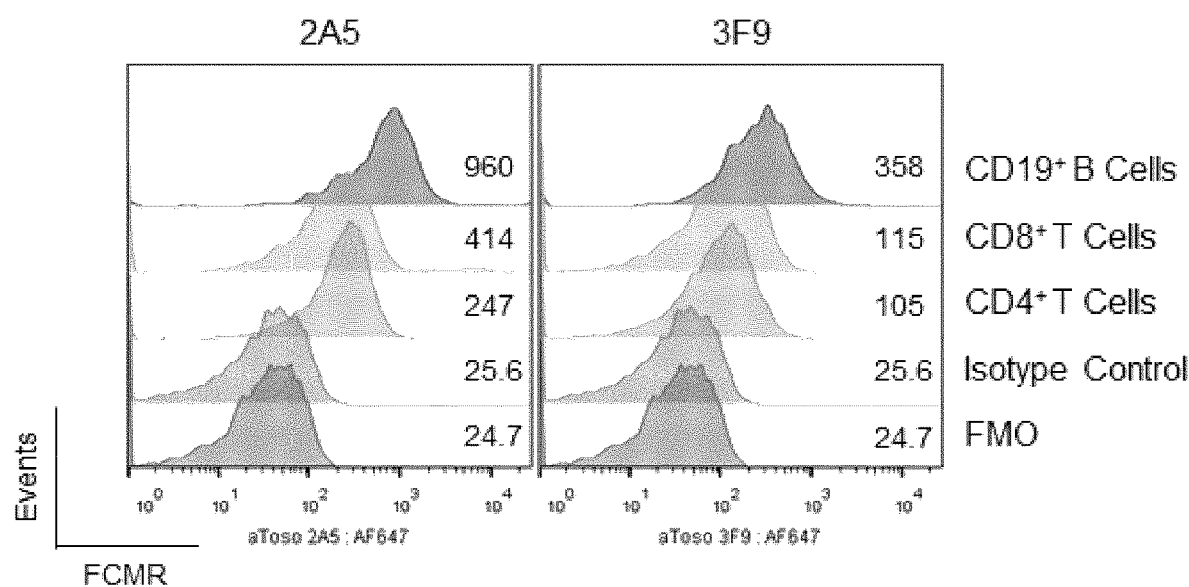
FIG. 1 shows FCMR surface expression on various hematopoietic subsets using flow cytometry.

The present disclosure provides novel anti-FCMR antibodies. The anti-FCMR antibodies described herein bind human FCMR. In some embodiments, the anti-FCMR antibodies bind human FCMR with high affinities. In some embodiments, the anti-FCMR antibodies stimulate an immune response. In some embodiments, the anti-FCMR antibodies suppress an immune response. Also provided in the present disclosure are methods of using such antibodies to modulate an immune response in a subject, and, for example, to treat cancer, an autoimmune disease, bacterial infection, or viral infection.

To facilitate an understanding of the present invention, a number of terms and phrases are defined below.

As used herein, each of the following terms has the meaning associated with it in this section.

As used herein, the term "FCMR", "Toso", "FAIM3" or "Fas apoptotic inhibitory molecule 3" refers to a protein having an amino acid sequence substantially identical to any of the representative Toso sequences, including any and all versions of GenBank Accession Nos. NP_001 135945 (human isoform b), NP_001 180267 (human isoform c), NP_005440 (human isoform a), NP_081252 (mouse) or NP_001014843 (rat). Suitable cDNA encoding Toso are provided at GenBank Accession Nos. NM_001 142473, NM_001 193338, NM_005449, NM_026976, and NM_001014843.

As used herein, the term "biological activity of FCMR" or "FCMR activity" refers to any biological activity associated with the full length native FCMR protein. In some embodiments, the biological activity of FCMR refers to binding to an IgM antibody. In further embodiments, the biological activity of FCMR refers to inhibiting CD11b or CD18 activity. In yet further embodiments, the biological activity of FCMR refers to increasing the activation threshold of granulocytes. Activation threshold can be measured by number of activated granulocytes from bone marrow. In further embodiments, the biological activity of FCMR includes the activation of dendritic cells and their ability to present antigen to T cells. In further embodiments, the biological activity of FCMR includes inhibition of apoptosis or enhancement of TNF signaling. In some embodiments, the FCMR biological activity is equivalent to the activity of a protein having an amino acid sequence represented by GenBank Accession No. NP_001 135945, NP_001 180267, NP 005440, NP_081252 or NP_001014843, including any and all versions of these accession numbers.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, more preferably ±5%, even more preferably ±1%, and still more preferably ±0.1% from the specified value, as such variations are appropriate to perform the disclosed methods.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, an "antigen binding domain" binds a target antigen as outlined herein. As is known in the art, these CDRs are generally present as a first set of variable heavy CDRs (vhCDRs or VHCDRs or CDR-HC) and a second set of variable light CDRs (vlCDRs or VLCDRs or CDR-LC), each comprising three CDRs: vhCDR1, vhCDR2, vhCDR3 for the heavy chain and vlCDR1, vlCDR2 and vlCDR3 for the light chain. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the VH and VL domains are covalently attached, generally through the use of a linker as outlined herein, into a single polypeptide sequence, which can be either (starting from the N-terminus) vh-linker-vl or vl-linker-vh, with the former being generally preferred (including optional domain linkers on each side, depending on the format used. As is understood in the art, the CDRs are separated by framework regions in each of the variable heavy and variable light domains: for the light variable region, these are FR1-vlCDR1-FR2-vlCDR2-FR3-vlCDR3-FR4, and for the heavy variable region, these are FR1-vhCDR1-FR2-vhCDR2-FR3-vhCDR3-FR4, with the framework regions showing high identity to human germline sequences. Antigen binding domains of the invention include, Fab, Fv and scFv.

By "linker" herein is meant a linker used in scFv and/or other antibody structures. Generally, there are a number of suitable scFv linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 4), glycine-alanine polymers, alanine-serine polymers, and other flexible linkers. Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers, that is may find use as linkers. Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR), hinge region-derived sequences, and other natural sequences from other proteins. In some embodiments, the linker is a "domain linker", used to link any two domains as outlined herein together. While any suitable linker can be used, many embodiments utilize a glycine-serine polymer, including for example (GS)n, (GSGGS)n, (GGGGS)n, and (GGGS)n, where n is an integer of at least one (and generally from 3 to 4 to 5) as well as any peptide sequence that allows for recombinant attachment of the two domains with sufficient length and flexibility to allow each domain to retain its biological function.

The term "antibody" is used in the broadest sense and includes, for example, an intact immunoglobulin or an antigen binding portion. Antigen binding portions may be produced by recombinant DNA techniques or by enzymatic or chemical cleavage of intact antibodies. Thus the term antibody includes traditional tetrameric antibodies of two heavy chains and two light chains, as well as antigen binding fragments such as Fv, Fab and scFvs. In some cases, the invention provides bispecific antibodies that include at least one antigen binding domain as outlined herein.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution M252Y refers to a variant polypeptide, in this case an Fc variant, in which the methionine at position 252 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "variant protein" or "protein variant", "variant" as used herein is meant a protein that differs from that of a parent protein by virtue of at least one amino acid modification. Protein variant may refer to the protein itself, a composition comprising the protein, or the amino acid sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4. The protein variant sequence herein will preferably possess at least about 80% identity with a parent protein sequence, and most preferably at least about 90% identity, more preferably at least about 95%-98%-99% identity. Variant protein can refer to the variant protein itself, compositions comprising the protein variant, or the DNA sequence that encodes it.

Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. For all positions discussed in the present invention that relate to antibodies, unless otherwise noted, amino acid position numbering is according to Kabat for the variable region numbering and is according to the EU index for the constant regions, including the Fc region. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids.

As used herein, "protein" herein is meant at least two covalently attached amino acids, which includes proteins, polypeptides, oligopeptides and peptides. The peptidyl group may comprise naturally occurring amino acids and peptide bonds.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein. By "Fv" or "Fv fragment" or "Fv region" as used herein is meant a polypeptide that comprises the VL and VH domains of a single antigen binding domain (ABD). As will be appreciated by those in the art, these generally are made up of two chains, or can be combined (generally with a linker as discussed herein) to form a scFv.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. In some cases, as outlined herein, binding to one or more of the FcγR receptors is reduced or ablated. For example, reducing binding to FcγRIIIa reduces ADCC, and in some cases, reducing binding to FcγRIIIa and FcγRIIb is desired.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "heavy constant region" herein is meant the CH1-hinge-CH2-CH3 portion of an antibody, generally from human IgG1, IgG2 or IgG4.

By "target antigen" as used herein is meant the molecule that is bound specifically by the variable region of a given antibody. In the present case, the target antigen is a BTLA protein.

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

By "position" as used herein is meant a location in the sequence of a protein. Positions may be numbered sequentially, or according to an established format, for example the EU index for antibody numbering.

By "residue" as used herein is meant a position in a protein and its associated amino acid identity. For example, Asparagine 297 (also referred to as Asn297 or N297) is a residue at position 297 in the human antibody IgG1.

The antibodies of the present invention are generally recombinant. "Recombinant" means the antibodies are generated using recombinant nucleic acid techniques in exogenous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

An example of an implementation of this algorithm to determine percent identity of a sequence is provided by the Genetics Computer Group (Madison, WI) in the "BestFit" utility application. The default parameters for this method are described in the Wisconsin Sequence Analysis Package Program Manual, Version 8 (1995) (available from Genetics Computer Group, Madison, WI). Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, CA). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In some embodiments, the $K_D$ of an antibody is determined by Bio-Layer Interferometry. In some embodiments, the $K_D$ value is measured with the immobilized. In other embodiments, the $K_D$ value is measured with the antibody (e.g., parent mouse antibody, chimeric antibody, or humanized antibody variants) immobilized. In certain embodiments, the $K_D$ value is measured in a bivalent binding mode. In other embodiments, the $K_D$ value is measured in a monovalent binding mode.

A "disease" includes a state of health of an animal, including a human, wherein the animal cannot maintain homeostasis, and wherein if the disease is not ameliorated then the animal's health continues to deteriorate.

In contrast, a "disorder" in an animal, including a human, includes a state of health in which the animal is able to maintain homeostasis, but in which the animal's state of health is less favorable than it would be in the absence of the disorder. Left untreated, a disorder does not necessarily cause a further decrease in the animal's state of health.

The terms "treatment", "treating", "treat", and the like, refer to obtaining a desired pharmacologic and/or physiologic effect. The effect may be prophylactic in terms of completely or partially preventing a disease or symptom thereof or reducing the likelihood of a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

As used herein, the term "mammal" refers to any mammal, including, but not limited to, mammals of the order Rodentia, such as mice and hamsters, and mammals of the order Logomorpha, such as rabbits. In some embodiments, the mammals are from the order Carnivora, including felines (cats) and canines (dogs). In some embodiments, the mammals are from the order Artiodactyla, including bovines (cows) and swines (pigs) or of the order Perssodactyla, including Equines (horses). It is most preferred that the mammals are of the order Primates, Ceboids, or Simoids (monkeys) or of the order Anthropoids (humans and apes). In some embodiments, the mammal is a human. In some embodiments, the mammal is cynomolgus monkey.

The term "regression," as well as words stemming therefrom, as used herein, does not necessarily imply 100% or complete regression. Rather, there are varying degrees of regression of which one of ordinary skill in the art recognizes as having a potential benefit or therapeutic effect. In this respect, the disclosed methods can provide any amount of any level of regression of a cancer in a mammal. Furthermore, the regression provided by the inventive method can include regression of one or more conditions or symptoms of the disease, e.g., a cancer. Also, for purposes herein, "regression" can encompass delaying the onset of the disease, delaying the onset of a symptom, and/or delaying the onset of a condition thereof. With respect to progressive diseases and disorders, "regression" can encompass slowing the progression of the disease or disorder, slowing the progression of a symptom of the disease or disorder, and/or slowing the progression of a condition thereof.

An "effective amount" or "therapeutically effective amount" of a composition includes that amount of the composition which is sufficient to provide a beneficial effect to the subject to which the composition is administered. An "effective amount" of a delivery vehicle includes that amount sufficient to effectively bind or deliver a composition.

By "individual" or "host" or "subject" or "patient" is meant any mammalian subject for whom diagnosis, treatment, or therapy is desired, particularly humans. Other subjects may include cynomolgus monkey, cattle, dogs, cats, guinea pigs, rabbits, rats, mice, horses, and so on.

The term "in combination with" as used herein refers to uses where, for example, a first therapy is administered during the entire course of administration of a second therapy; where the first therapy is administered for a period of time that is overlapping with the administration of the second therapy, e.g., where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

"Encoding" includes the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if, for example, transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

The term "operably linked" as used herein includes a polynucleotide in functional relationship with a second polynucleotide, e.g., a single-stranded or double-stranded nucleic acid moiety comprising the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. The order specified when indicating operably linkage is not important. For example, the phrases: "the promoter is operably linked to the nucleotide sequence" and "the nucleotide sequence is operably linked to the promoter" are used interchangeably herein and are considered equivalent. In some cases, when the nucleic acid encoding the desired protein further comprises a promoter/regulatory sequence, the promoter/regulatory sequence is positioned at the 5' end of the desired protein coding sequence such that it drives expression of the desired protein in a cell.

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

The term "recombinant," as applied to a polynucleotide means the polynucleotide is the product of various combinations of cloning, restriction or ligation steps, and other procedures resulting in a construct distinct and/or different from a polynucleotide found in nature. The terms respectively include replicates of the original polynucleotide construct and progeny of the original virus construct.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors.

A "vector" is capable of transferring gene sequences to target-cells. Typically, "vector construct," "expression vector," and "gene transfer vector," mean any nucleic acid construct capable of directing the expression of a gene of interest and which can transfer gene sequences to target-cells, which can be accomplished by genomic integration of all or a portion of the vector, or transient or inheritable maintenance of the vector as an extrachromosomal element. Thus, the term includes cloning, and expression vehicles, as well as integrating vectors.

The term "regulatory element" as used herein includes a nucleotide sequence which controls some aspect of the expression of nucleic acid sequences. Examples of regulatory elements illustratively include an enhancer, an internal ribosome entry site (IRES), an intron, an origin of replication, a polyadenylation signal (pA), a promoter, an enhancer, a transcription termination sequence, and an upstream regulatory domain, which contribute to the replication, transcription, and/or post-transcriptional processing of a nucleic acid sequence. In cases, regulatory elements can also include cis-regulatory DNA elements as well as transposable elements (TEs). Those of ordinary skill in the art are capable of selecting and using these and other regulatory elements in an expression construct with no more than routine experimentation. Expression constructs can be generated using a genetic recombinant approach or synthetically using well-known methodology.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

The statement that an amino acid residue is "phosphorylated" used herein means that a phosphate group is ester-linked to the side chain of the amino acid residue. Typical amino acid residues that may be phosphorylated include serine (Ser), threonine (Thr), and tyrosine (Tyr).

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

Various aspects of the invention are set forth below in sections; however, aspects of the invention described in one particular section are not to be limited to any particular section.

I. Antibodies

The present disclosure provides novel anti-FCMR antibodies. Such antibodies bind human FCMR. Table 1 lists peptide sequences of heavy chain variable regions and light chain variable regions that, in combination as designated in Table 1, can bind to human FCMR. In some embodiments, the heavy chain variable region and the light chain variable region are arranged in a Fab format. In some embodiments, the heavy chain variable region and the light chain variable region are fused together to from an scFv.

Mouse antibodies directed against human FCMR were generated using conventional mouse monoclonal antibody techniques. Briefly, mice (strain SJL/J) were inoculated with recombinant human FCMR-Fc. After boosting, antibody titers were determined by ELISA, using a non-relevant His6-tagged protein as a control. Mice selected for fusion were sacrificed and hybridoma fusion was performed using the P3X63Ag8.653 murine myeloma cell line as a fusion partner. Clones were isolated by limiting dilution and selected by ELISA of hybridoma supernatants. Recombinant human FCMR-Fc was used as a substrate for ELISA assays.

Hybridoma mRNA was transcribed to cDNA and amplified by 5'-rapid amplification of cDNA ends (RACE). PCR products were cloned into an appropriate sequencing vector and sequenced by the dideoxy Sanger method. Multiple copies were sequenced to verify the clonality of each clone. Translated protein sequences were entered into the NCBI IgBLAST search tool (Ye, J., et al., 2013, Nucleic Acids Res. 41, W34-40) to identify CDRs.

TABLE 1

| Clone | Heavy chain variable region amino acid sequence | Light chain variable region amino acid sequence (kappa) |
|---|---|---|
| 2A5 | MNFGLSLIFLALILKGVQCEVQL VESGGDLVKPGGSLKLSCAASG FTFSSYGMSWVRQTPDKRLEW VATINSGGSSIYYPDSVKGRFTIS RDNAKNTLYLQMSSLKSEDTA MYYCARHNDSSYRYAMDYW GQGTSVTVSSAKTT SEQ ID NO: 1 (IgG2b) CDR1 (SEQ ID NO: 13)- GFTFSSYG CDR2 (SEQ ID NO: 14)- INSGGSSI CDR3 (SEQ ID NO: 15)- ARHNDSSYRYAMDY | MRTPAQFLGILLLWFPGIKCDI KMTQSPSSMYASLGERVTITC KASQDINNFLSWFQQKPGKSP KTLIYRANGLVDGVPSRFSGS GSGQDYSLTISSLEYEDMGIY YCLQYDEFPPTFGGGTKLEFK RADA SEQ ID NO: 2 (kappa) CDR1 (SEQ ID NO: 16)- QDINNF CDR2 (SEQ ID NO: 17)-RAN CDR3 (SEQ ID NO: 18)- LQYDEFPPT |
| 2H2 | MNFGLSLIFLALILKGVQCEVQL VESGGDLVKPGGSLKPSCAASG FSFSSYGMSWVRQTPDKRLEWV ATISSGGSNIQYLDSVKGRFTISR DNAKNTLYLQMSSLKSEDTAM YYCVRHDDGSSYQYAMDYWG QGTSVTVSSAKTTPPSVYPLAPG SAAQTNSMVTLGCLVKGYFPEP VTVTWNSGSLSSGVHTFPAVLQ SDLYTLSSSVTVPSSTWPSQTVT CNVAHPASSTKVDKKIVPRDCG CKPCICTVPEVSSVFIPPPKPKDV LTITLTPKVTCVVVDISKDDQG SEQ ID NO: 3 (IgG1) CDR1 (SEQ ID NO: 19)- GFSFSSYG CDR2 (SEQ ID NO: 20)-SSGGSNI CDR3 (SEQ ID NO: 21)- VRHDDGSSYQYAMDY | MDMRTPAQFLGILLLWFPGIK CDIKMTQSPSSMYASLGERVT ITCKASQDINSYLSWFQQKPG KSPKTLIYRANRLVDGVPSRF SGSGSGQDLSLTISSLEYEDM GIYYCLQYDEFPLTFGAGTKL ELKRADAAPTVSIFPPSSEQLT SGGASVVCFLNNFYPRDINVK WKIDGSERQNGVLNSWTDQD SKDSTYSMSSTLTLTKDEYER HNSYTCEATHKTSTSP SEQ ID NO: 4 (kappa) CDR1 (SEQ ID NO: 22)- QDINSY CDR2 (SEQ ID NO: 23)-RAN CDR3 (SEQ ID NO: 24)- LQYDEFPLT |
| 6D6 | MNFGLSLIFLALILKGVQCEVQL VESGGDLVKPGGSLKLSCAASG FTFSSYGMSWVRQTPDKRLEW VATISSGGTYNSYLDSVKGRFTI SRDNAKNTLYLQMSSLKSEDTA MYYCARHDDGSRYQYIVDYWG QGTSVTVSSAKTTPPSVYPLAPG SAAQTNSMVTLGCLVKGYFPEP VTVTWNSGSLSSGVHTFPAVLQ SDLYTLSSSVTVPSSTWPSQTVT CNVAHPASSTKVDKKIVPRDCG CKPCICTVPEVSSVFIPPPKPKDV LTITLTPKVTC SEQ ID NO: 5 (IgG1) CDR1 (SEQ ID NO: 25)- GFTFSSYG CDR2 (SEQ ID NO: 26)- ISSGGTYN CDR3 (SEQ ID NO: 27)- ARHDDGSRYQYIVDY | MDMRTPAQFLGILLLWFPGIK CDIKMTQSPSSMYASLGERVT ITCKASQDINSYLSWFQQKPG KSPKTLIYRANRLVDGVPSRF SGSGSGQDYSLTISSLEYEDM GIYYCLQYDEFPLTFGAGTKL ELKRADAAPTVSIFPPSSEQLT SGGASVVCFLNNFYPRDINVK WKIDGSERQNGVLNSWTDQD SKDSTYSMSSTLTLTKDEYER HNSYTCEATHKTSTSP VVDISKDDQ SEQ ID NO: 6 (kappa) CDR1 (SEQ ID NO: 28)- QDINSY CDR2 (SEQ ID NO: 29)-RAN CDR3 (SEQ ID NO: 30)- LQYDEFPLT |
| 1F5 | MGWSWIFLFLLSGTAGVLSEVQ LQQSGPELVKPGASVKISCKASG YTFTDYYINWVKQSHGKSLEWI GDVYPNNGGTSYNQFKDKAT LTVDKSSNTAYMELRSLTSADS AVYYCARQLTYWGRGTLVTVS AAKTTPPSVYPLAPGSAAQTNS MVTLGCLVKGYFPEPVTVTWNS GSLSSGVHTFPAVLQSDLYTLSS SVTVPSSTWPSQTVTCNVAHPA SSTKVDKKIVPRDCGCKPCICTV PEVSSVFIPPPKPKDVLTITLTPK VTCVVVDISKDDQG SEQ ID NO: 7 (IgG1) CDR1 (SEQ ID NO: 31)- GYTFTDYY CDR2 (SEQ ID NO: 32)- VYPNNGGT CDR3 (SEQ ID NO: 33)-ARQLTY | MESQTQVLISLLFWVSGTCGD IVMTQSPSSLSVSAGEKVTMS CKASQSLLKSGKQENYLAWY QQKPGLPPKVLIYGASTRESG VPDRFTGSGSGTDFTLTISSVQ AEDLAVYYCQNDHSYPLTFG AGTKLELKRADAAPTVSIFPP SSEQLTSGGASVVCFLNNFYP RDINVKWKIDGSERQNGVLN SWTDQDSKDSTYSMSSTLTLT KDEYERHNSYTCEATHKTSTS P SEQ ID NO: 8 (kappa) CDR1 (SEQ ID NO: 34)- QSLLKSGKQENY CDR2 (SEQ ID NO: 35)-GAS CDR3 (SEQ ID NO: 36)- QNDHSYPLT |

TABLE 1-continued

| Clone | Heavy chain variable region amino acid sequence | Light chain variable region amino acid sequence (kappa) |
|---|---|---|
| 1G4/5D10/ 5E12/9D7/ 10D10 | MGWSCIILFLVATATGVHSQVQ LQQPGAELVRPGSSVKLSCKAS GYTFTNHWLHWVKQRPIQGLE WIGYIDPSDSLTHYNQNFKDKA TLTVDKSSSTAYMQLSSLTSEDS AVYYCARFSFAYWGQGTLVTV SAAKTTPPSVYPLAPGSAAQTNS MVTLGCLVKGYFPEPVTVTWNS GSLSSGVHTFPAVLQSDLYTLSS SVTVPSSTWPSQTVTCNVAHPA SSTKVDKKIVPRDCGCKPCICTV PEVSSVFIPPPKPKDVLTITLTPK VTCVVVDISKDDQG SEQ ID NO: 9 (IgG1) CDR1 (SEQ ID NO: 37)- GYTFTNHW CDR2 (SEQ ID NO: 38)- IDPSDSLT CDR3 (SEQ ID NO: 39)-ARFSFAY | MMSPAQFLFLLVLWIRETNG DVVMTQTPLTLSVTIGQPASIS CKSSQSLLDSDGKTYLNWLL QRPGQSPKRLIYLVSKLDSGV PDRFTGSGSGTDFTLKISRVE AEDLGVYYCWQGTHLWTFG GGTKLEIKRADAAPTVSIFPPS SEQLTSGGASVVCFLNNFYPR DINVKWKIDGSERQNGVLNS WTDQDSKDSTYSMSSTLTLT KDEYERHNSYTCEATHKTSTS P SEQ ID NO: 10 (kappa) CDR1 (SEQ ID NO: 40)- QSLLDSDGKTY CDR2 (SEQ ID NO: 41)-LVS CDR3 (SEQ ID NO: 42)- WQGTHLWTF |
| 3F9 | MGWSWIFLFLLSGTAGVLSEVQ LQQSGPELVKPGASVKISCKASG YTFTDYYINWVKQSHGKSLEWI GDIYPNNGGTNYNQKFKGKATL TVDKSSSTAYMELRSLTSEDSA VYYCARQLTYWGPGTLVTVSA AKTTPPSVYPLAPGCGDTTGSSV TLGCLVKGYFPESVTVTWNSGS LSSSVHTFPALLQSGLYTMSSSV TVPSSTWPSQTVTCSVAHPASST TVDKKLEPSGPISTINPCPPCKEC HKCPAPNLEGGPSVFIFPPNIKD VLMISLTPKVTCVVVDVSEDDQ G SEQ ID NO: 11 (IgG2b) CDR1 (SEQ ID NO: 43)- GYTFTDYY CDR2 (SEQ ID NO: 44)- IYPNNGGT CDR3 (SEQ ID NO: 45)-ARQLTY | MESQTQVLISLLFWVSGTCGD IVMTQSPSSLSVSVGEKVTMN CKSSQSLLNSGHQENYLAWY QQKPGQPPKVLIYGAVTRESG VPDRFTGSGSGTDFTLTISSVQ AEDLAVYYCQNDHSYPLTFG AGTKLELKRADAAPTVSIFPP SSEQLTSGGASVVCFLNNFYP RDINVKWKIDGSERQNGVLN SWTDQDSKDSTYSMSSTLTLT KDEYERHNSYTCEATHKTSTS P SEQ ID NO: 12 (kappa) CDR1 (SEQ ID NO: 46)- QSLLNSGHQENY CDR2 (SEQ ID NO: 47)-GAV CDR3 (SEQ ID NO: 48)- QNDHSYPLT |

In some embodiments, the anti-FCMR antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:2.

In some embodiments, the anti-FCMR antibodies include a vhCDR1 comprising SEQ ID NO:13, a vhCDR2 comprising SEQ ID NO:14, a vhCDR3 comprising SEQ ID NO:15, a vlCDR1 comprising SEQ ID NO:16, a vlCDR2 comprising amino acid sequence RAN, and a vlCDR3 comprising SEQ ID NO:18. In some embodiments, one or more of such 6 CDRs have from 1, 2, 3, 4 or 5 amino acid modifications. In further embodiments, a single CDR contains 1 or 2 amino acid substitutions, and the modified anti-FCMR antibodies retain binding to human FCMR.

In some embodiments, the anti-FCMR antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:3 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:4.

In some embodiments, the anti-FCMR antibodies include a vhCDR1 comprising SEQ ID NO:19, a vhCDR2 comprising SEQ ID NO:20, a vhCDR3 comprising SEQ ID NO:21, a vlCDR1 comprising SEQ ID NO:22, a vlCDR2 comprising amino acid sequence RAN, and a vlCDR3 comprising SEQ ID NO:24. In further embodiments, a single CDR contains 1 or 2 amino acid substitutions, and the modified anti-FCMR antibodies retain binding to human FCMR.

In some embodiments, the anti-FCMR antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:5 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:6.

In some embodiments, the anti-FCMR antibodies include a vhCDR1 comprising SEQ ID NO:25, a vhCDR2 comprising SEQ ID NO:26, a vhCDR3 comprising SEQ ID NO:27, a vlCDR1 comprising SEQ ID NO:28, a vlCDR2 comprising amino acid sequence RAN, and a vlCDR3 comprising SEQ ID NO:30. In some embodiments, one or more of such 6 CDRs have from 1, 2, 3, 4 or 5 amino acid modifications. In further embodiments, a single CDR contains 1 or 2 amino acid substitutions, and the modified anti-FCMR antibodies retain binding to human FCMR.

In some embodiments, the anti-FCMR antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:7 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:8.

In some embodiments, the anti-FCMR antibodies include a vhCDR1 comprising SEQ ID NO:31, a vhCDR2 comprising SEQ ID NO:32, a vhCDR3 comprising SEQ ID NO:33, a vlCDR1 comprising SEQ ID NO:34, a vlCDR2 comprising amino acid sequence GAS, and a vlCDR3 comprising SEQ ID NO:36. In some embodiments, one or more of such 6 CDRs have from 1, 2, 3, 4 or 5 amino acid modifications. In further embodiments, a single CDR contains 1 or 2 amino acid substitutions, and the modified anti-FCMR antibodies retain binding to human FCMR.

In some embodiments, the anti-FCMR antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:9 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 10.

In some embodiments, the anti-FCMR antibodies include a vhCDR1 comprising SEQ ID NO:37, a vhCDR2 comprising SEQ ID NO:38, a vhCDR3 comprising SEQ ID NO:39, a vlCDR1 comprising SEQ ID NO:40, a vlCDR2 comprising amino acid sequence LVS, and a vlCDR3 comprising SEQ ID NO:42. In some embodiments, one or more of such 6 CDRs have from 1, 2, 3, 4 or 5 amino acid modifications. In further embodiments, a single CDR contains 1 or 2 amino acid substitutions, and the modified anti-FCMR antibodies retain binding to human FCMR.

In some embodiments, the anti-FCMR antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:11 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 12.

In some embodiments, the anti-FCMR antibodies that include a vhCDR1 comprising SEQ ID NO:43, a vhCDR2 comprising SEQ ID NO:44, a vhCDR3 comprising SEQ ID NO:45, a vlCDR1 comprising SEQ ID NO:46, a vlCDR2 comprising amino acid sequence GAV, and a vlCDR3 comprising SEQ ID NO:48. In some embodiments, one or more of such 6 CDRs have from 1, 2, 3, 4 or 5 amino acid modifications. In further embodiments, a single CDR contains 1 or 2 amino acid substitutions, and the modified anti-FCMR antibodies retain binding to human FCMR.

In addition to the sequence variants described herein in the heavy chain and light chain variable regions and/or CDRs, changes in the framework region(s) of the heavy and/or light variable region(s) can be made. In some embodiment, variants in the framework regions (e.g., excluding the CDRs) retain at least about 80, 85, 90 or 95% identity to a germline sequence. Variants can be made to retain at least about 80, 85, 90 or 95% identity to any one of the light chain V-GENE, light chain J-GENE, heavy chain V-GENE, heavy chain J-GENE, and heavy chain D-GENE alleles.

In some embodiments, variations are made in the framework regions that retain at least 80, 85, 90 or 95% identity to a germline gene sequence, while keeping 6 CDRs unchanged.

In some embodiments, variations are made in both the framework regions that retain at least 80, 85, 90 or 95% identity to a germline gene sequence, and the 6 CDRs. The CDRs can have amino acid modifications (e.g., from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.).

By selecting amino acid sequences of CDRs and/or variable regions of a heavy chain and a light chain from those described herein and combining them with amino acid sequences of framework regions and/or constant regions of a heavy chain and a light chain of an antibody as appropriate, a person skilled in the art will be able to design an anti-FCMR antibody according to the present invention. The antibody framework regions and/or constant region (Fc domain) described in the current invention can derive from an antibody of any species, such as from human, rabbit, dog, cat, mouse, horse or monkey.

In some embodiments, the constant region is derived from human, and includes a heavy chain constant region derived from those of IgG, IgA, IgM, IgE, and IgD subtypes or variants thereof, and a light chain constant region derived from kappa or lambda subtypes or variants thereof. In some embodiments, the heavy chain constant region is derived from a human IgG, including IgG1, IgG2, IgG3, and IgG4. In some embodiments, the amino acid sequence of the heavy chain constant region is at least 80%, 85%, 90%, or 95% identical to a human IgG1, IgG2, IgG3, or IgG4 constant region. In some other embodiments, the amino acid sequence of the constant region is at least 80%, 85%, 90%, or 95% identical to an antibody constant region from another mammal, such as rabbit, dog, cat, mouse, horse or monkey. In some embodiments, the antibody constant region includes a hinge, a CH2 domain, a CH3 domain and optionally a CH1 domain.

In some embodiments, the antibodies described herein can be derived from a mixture from different species, e.g., forming a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system, as described for example in Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci, USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. Other humanization methods may involve the grafting of only parts of the CDRs, including but not limited to methods described in Tan et al., 2002, J. Immunol. 169:1119-1125; De Pascalis et al., 2002, J. Immunol. 169:3076-3084, all entirely incorporated by reference.

In some embodiments, the antibodies of the current invention comprise a heavy chain variable region derived from a particular human germline heavy chain immunoglobulin gene and/or a light chain variable region derived from a particular human germline light chain immunoglobulin gene. Such antibodies may contain amino acid differences as compared to the human germline sequences, due to, for example, naturally-occurring somatic mutations or intentional introduction of site-directed mutation. However, a humanized antibody typically is at least 80% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the human germline immunoglobulin gene. Typically, a humanized antibody derived from a particular human germline sequence will display no more than 10-20 amino acid differences from the amino acid sequence encoded by the human germline immunoglobulin gene. In certain cases, the humanized antibody may display no more than 5, or even no more than 4, 3, 2, or 1 amino acid difference from the amino acid sequence encoded by the germline immunoglobulin gene.

In some embodiments, the antibodies of the current disclosure are humanized and affinity matured, as is known in the art. Structure-based methods may be employed for humanization and affinity maturation, for example as described in U.S. Pat. No. 7,657,380. Selection based methods may be employed to humanize and/or affinity mature antibody variable regions, including but not limited to methods described in Wu et al., 1999, J. Mol. Biol. 294: 151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10): 753-759, all entirely incorporated by reference.

II. Characteristics of the Antibodies

In some embodiments, the anti-FCMR antibodies described herein bind to human FCMR. In some embodiments, binding of the anti-FCMR antibodies to human FCMR is measured by flow cytometry, such as the exemplary assay described in Example 1.

In some embodiments, the anti-FCMR antibodies described herein bind human FCMR with high affinities. In further embodiments, antibodies with high affinities are those with affinities in the nanomolar or picomolar range. In some embodiments, the anti-FCMR antibodies described herein have high binding affinity to FCMR-Fc protein (see FIG. 6). The $K_D$ value can be measured with the antigen immobilized or with the antibody immobilized. FIG. 6 lists exemplary $K_D$s of some of the antibody clones. In some embodiments, the $K_D$ values between the antibodies and human FCMR range from $2.57 \times 10^{-8}$ M to $7.21 \times 10^{-9}$ M.

In some embodiments, the anti-FCMR antibodies display low immunogenicity when administered into human subjects. These antibodies can contain an Fc domain derived from human IgG1, human IgG2 or human IgG3. In some embodiments, these antibodies are humanized using the framework regions derived from human immunoglobulins.

Effects of the anti-FCMR antibodies on cytokine release can be assayed using a variety of methods known in the art and described herein, including for example, by the method described in Examples 4 and 5. Accordingly, the anti-FCMR antibodies can serve as FCMR antagonists or FCMR agonists.

In some embodiments, anti-FCMR antibodies described act as FCMR antagonists, and inhibit T cell function. As a result, such anti-FCMR antibodies suppress an immune response. Examples of such anti-FCMR antibodies include antibodies that contain a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:9, and a light chain variable region comprising amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 10; and/or a vhCDR1 comprising SEQ ID NO:37, a vhCDR2 comprising SEQ ID NO:38, a vhCDR3 comprising SEQ ID NO:39, a vlCDR1 comprising SEQ ID NO:40, a vlCDR2 comprising amino acid sequence LVS, and a vlCDR3 comprising SEQ ID NO:42

In some other embodiments, anti-FCMR antibodies described herein act as FCMR agonists, and stimulate immune cell functions, including pro-inflammatory T cell functions. As a result, such anti-FCMR antibodies stimulate an immune response. For example, such anti-FCMR antibodies can include a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:2; and/or a vhCDR1 comprising SEQ ID NO:13, a vhCDR2 comprising SEQ ID NO:14, a vhCDR3 comprising SEQ ID NO:15, a vlCDR1 comprising SEQ ID NO:16, a vlCDR2 comprising amino acid sequence RAN, and a vlCDR3 comprising SEQ ID NO:18.

III. Nucleic Acids of the Invention

Nucleic acids encoding the anti-FCMR antibodies described herein are also provided, as well as expression vectors containing such nucleic acids and host cells transformed with such nucleic acids and/or expression vectors. As will be appreciated by those in the art, the protein sequences depicted herein can be encoded by any number of possible nucleic acid sequences due to the degeneracy of the genetic code.

As will be appreciated by those in the art, in the case of antigen binding domains, the nucleic acid compositions generally include a first nucleic acid encoding the heavy chain variable region and a second nucleic acid encoding the light chain variable region. In the case of scFvs, a single nucleic acid encoding the heavy chain variable region and light chain variable region, separated by a linker described herein, can be made. In the case of traditional antibodies, the nucleic acid compositions generally include a first nucleic acid encoding the heavy chain and a second nucleic acid encoding the light chain, which will, upon expression in a cell, spontaneously assemble into the "traditional" tetrameric format of two heavy chains and two light chains.

As is known in the art, the nucleic acids encoding the components of the invention can be incorporated into expression vectors, and depending on the host cells, used to produce the antibodies of the invention. These two nucleic acids can be incorporated into a single expression vector or into two different expression vectors. Generally, the nucleic acids can be operably linked to any number of regulatory elements (promoters, origin of replication, selectable markers, ribosomal binding sites, inducers, etc.) in an expression vector. The expression vectors can be extra-chromosomal or integrating vectors.

The nucleic acids and/or expression vectors of the current invention can be introduced into any type of host cells, which are well known in the art, including mammalian, bacterial, yeast, insect and fungal cells. After transfection, single cell clones can be isolated for cell bank generation using methods known in the art, such as limited dilution, ELISA, FACS, microscopy, or Clonepix. Clones can be cultured under conditions suitable for bio-reactor scale-up and maintained expression of the antibodies. The antibodies can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

IV. Therapeutic Applications

The current disclosure provides a method of modulating an immune response in a subject, and the method includes administering to the subject an effective amount of an anti-FCMR antibody described herein, or a pharmaceutical composition containing an anti-FCMR antibody.

In some embodiments, the methods of modulating an immune response encompassed by the present disclosure comprises suppressing an immune response in a subject, and in further embodiments, such methods comprise administering to the subject an effective amount of an anti-FCMR antibody or by administering a pharmaceutical composition containing an anti-FCMR antibody.

In some embodiments, the methods of modulating an immune response encompassed by the present disclosure comprises stimulating an immune response in a subject, and in further embodiments, such methods comprise administering to the subject an effective amount of an anti-FCMR antibody or by administering a pharmaceutical composition containing an anti-FCMR antibody.

In some embodiments, the methods encompassed by the present disclosure comprise methods of modulating an immune response in a subject, for example, by administering anti-FCMR antibodies that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1, and a light chain variable region comprising amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 2; and/or a vhCDR1 comprising SEQ ID NO:13, a vhCDR2 comprising SEQ ID NO:14, a vhCDR3 comprising SEQ ID NO:15, a vlCDR1 comprising SEQ ID NO:16, a vlCDR2 comprising amino acid sequence RAN, and a vlCDR3 comprising SEQ ID NO:18.

In some embodiments, the methods described herein modulate an immune response in the subject, for example, by administering anti-FCMR antibodies that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:3 and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:4; and/or vhCDR1 comprising SEQ ID NO:19, a vhCDR2 comprising SEQ ID NO:20, a vhCDR3 comprising SEQ ID NO:21, a vlCDR1 comprising SEQ ID NO:22, a vlCDR2 comprising amino acid sequence RAN, and a vlCDR3 comprising SEQ ID NO:24.

In some embodiments, the methods described herein modulate an immune response in the subject, for example, by administering anti-FCMR antibodies that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:5, and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:6; and/or a vhCDR1 comprising SEQ ID NO:25, a vhCDR2 comprising SEQ ID NO:26, a vhCDR3 comprising SEQ ID NO:27, a vlCDR1 comprising SEQ ID NO:28, a vlCDR2 comprising amino acid sequence RAN, and a vlCDR3 comprising SEQ ID NO:30.

In some embodiments, the methods described herein modulate an immune response in the subject, for example, by administering anti-FCMR antibodies that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:7, and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:8; and/or a vhCDR1 comprising SEQ ID NO:31, a vhCDR2 comprising SEQ ID NO:32, a vhCDR3 comprising SEQ ID NO:33, a vlCDR1 comprising SEQ ID NO:34, a vlCDR2 comprising amino acid sequence GAS, and a vlCDR3 comprising SEQ ID NO:36.

In some embodiments, the methods described herein modulate an immune response in the subject, for example, by administering anti-FCMR antibodies that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:9, and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 10; and/or a vhCDR1 comprising SEQ ID NO:37, a vhCDR2 comprising SEQ ID NO:38, a vhCDR3 comprising SEQ ID NO:39, a vlCDR1 comprising SEQ ID NO:40, a vlCDR2 comprising amino acid sequence LVS, and a vlCDR3 comprising SEQ ID NO:42.

In some embodiments, the methods described herein modulate an immune response in the subject, for example, by administering anti-FCMR antibodies that includes a heavy chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:11, and a light chain variable region comprising an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 12; and/or a vhCDR1 comprising SEQ ID NO:43, a vhCDR2 comprising SEQ ID NO:44, a vhCDR3 comprising SEQ ID NO:45, a vlCDR1 comprising SEQ ID NO:46, a vlCDR2 comprising amino acid sequence GAV, and a vlCDR3 comprising SEQ ID NO:48.

The present disclosure also provides methods of treating cancer in a subject, and such methods include administering to the subject an effective amount of an anti-FCMR antibody or a pharmaceutical composition containing such anti-FCMR antibody. In some embodiments, the cancer to be treated expresses FCMR on the cancer cell surface. In some embodiments, the cancer to be treated upregulates FCMR compared to the corresponding non-cancerous tissue. In some embodiments, the cancer to treated is non-responsive to existing immune-modulating antibodies targeting other immune checkpoints, such as CTLA-4, PD-1 or PD-L1.

In some embodiments, the cancer is B-cell chronic lymphocytic leukemia, Hodgkin's lymphoma, B-cell non-Hodgkin's lymphoma or T-cell non-Hodgkin's lymphomas. In some embodiments, the cancer is a solid tumor, such as gastric cancer, colorectal cancer, hepatocellular carcinoma, melanoma, or esophageal squamous cell carcinoma.

In some other embodiments, the cancer is brain cancer, bladder cancer, breast cancer, cervical cancer, endometrial cancer, esophageal cancer, leukemia, lung cancer, liver cancer, melanoma, ovarian cancer, pancreatic cancer, prostate cancer, rectal cancer, renal cancer, testicular cancer, or uterine cancer. In yet other embodiments, the cancer is a vascularized tumor, squamous cell carcinoma, adenocarcinoma, small cell carcinoma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well-differentiated carcinoma, or Wilms tumor.

In some other embodiments, the cancer to be treated is a non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non- Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The present disclosure also provides methods of treating autoimmune or inflammatory disorders in a subject, and the method includes administering to the subject an effective amount of an anti-FCMR antibody or a pharmaceutical composition containing such anti-FCMR antibody. Administering an anti-FCMR antibody can suppress autoreactive immune responses in the subject suffering from an autoimmune or inflammatory disorder.

In some embodiments, the autoimmune or inflammatory disorder to treated is multiple sclerosis, Addison's disease, amyotrophic lateral sclerosis, Crohn's disease, Cushing's Syndrome, diabetes mellitus type 1, graft versus host disease, Graves' disease, Guillain-Barre syndrome, lupus erythematosus, psoriasis, psoriatic arthritis, rheumatoid arthritis, sarcoidosis, scleroderma, systemic lupus erythematosus, transplant rejection, or vasculitis.

In some other embodiments, the autoimmune or inflammatory disorder to be treated include, but are not limited to, Acute disseminated encephalomyelitis (ADEM), Agammaglobulinemia, Alopecia areata, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Cutaneous leukocytoclastic angiitis, Dego's disease, Dercum's disease, Dermatitis herpetiformis, Dermatomyositis, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Meniere's disease, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatica, Polymyositis, Primary biliary cirrhosis, Primary sclerosing cholangitis, Progressive inflammatory neuropathy, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Schizophrenia, Schmidt syndrome, Schnitzler syndrome, Scleritis, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vitiligo, Wegener's granulomatosis.

The present disclosure also provides methods of treating bacterial infections in a subject, and the method includes administering to the subject an effective amount of an anti-FCMR antibody that acts as a FCMR agonist, or a pharmaceutical composition containing such anti-FCMR antibody. Administering an anti-FCMR antibody can stimulate an inflammatory immune response to increase clearance of a bacterial infection.

In some embodiments, bacterial infections to be treated include but are not limited to: respiratory tract infections, acute bacterial otitis media, bacterial pneumonia, urinary tract infections, complicated infections, noncomplicated infections, pyelonephritis, intra-abdominal infections, deep-seated abscesses, bacterial sepsis, skin and skin structure infections, soft tissue infections, bone and joint infections, central nervous system infections, bacteremia, wound infections, peritonitis, meningitis, infections after burn, urogenital tract infections, gastro-intestinal tract infections, pelvic inflammatory disease, endocarditis, and other intravascular infections.

The present disclosure also provides methods of treating viral infections in a subject, and the method includes administering to the subject an effective amount of an anti-FCMR antibody that acts as a FCMR antagonist, or a pharmaceutical composition containing such anti-FCMR antibody. Administering an anti-FCMR antibody can stimulate an inflammatory immune response to increase clearance of a viral infection.

V. Combination Therapy

Anti-FCMR antibodies described herein can be used in combination with additional therapeutic agents to treat cancer or autoimmune disorders.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM-3, such as Ipilimumab, Nivolumab, Pembrolizumab, Avelumab, Durvalumab, and Atezolizumab.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Antibodies of the invention can also be used as an adjunct to surgical removal of cancer from the primary lesion.

Exemplary therapeutic agents that may be used as a part of a combination therapy with the anti-FCMR antibodies for treating, delaying the progression of, preventing a relapse of, or alleviating a symptom of an autoimmune or inflammatory disorder, include, for example, any of a variety of known anti-inflammatory and/or immunosuppressive therapy. In some embodiments, the anti-inflammatory and/or immunosuppressive therapies include, but are not limited to methotrexate, cyclosporin A (including, for example, cyclosporin microemulsion), tacrolimus, corticosteroids, statins, interferon beta, non-steroidal anti-inflammatory agents, and 6-MP (Mercaptopurine, also called 6-Mercaptopurine, or Purinethol).

In some embodiments, the anti-inflammatory and/or immunosuppressive therapies for combining with the anti-FCMR antibodies include, but are not limited to a TOPK inhibitor (e.g., OTS964 ((R)-9-(4-(1-(dimethylamino)propan-2-yl)phenyl)-8-hydroxy-6-methylthieno[2,3-c]quinolin-4(5H)-one) (Oncotherapy Science)), a tyrosine kinase inhibitor (e.g., axitinib, dasatinib, icotinib), a topoisomerase inhibitor (e.g., topotecan), a sphingosine-1-phosphate receptor agonist (e.g., fingolimod, KRP-203), anti-T cell immunoglobulin (e.g. AtGam), anti-IL-2 receptor antibody (e.g. daclizumab), amides (CTX), ifosfamide (IFO), adriamycin (ADM), daunorubicin (DNR), vincristine (VCR), vinblastine (VBL), etoposide (VP16), vermeer (Vumon), carboplatin (CBP), tacrolimus, sirolimus, everolimus, azathioprine, brequinar, leflunomide, LEA-29Y, anti-CD3 antibody (e.g. OKT3), aspirin, B7-CD28 blocking molecules (e.g. belatacept, abatacept), CD40-CD154 blocking molecules (anti-CD40 antibodies), acetaminophen, ibuprofen, naproxen, piroxicam, and anti-inflammatory steroids (e.g. prednisolone or dexamethasone).

In some embodiments, the anti-inflammatory and/or immunosuppressive therapies for combining with the anti-FCMR antibodies include ablation of autoimmune cells, for example, by administration of TNF-alpha, CFA, interleukin-1 (IL-1), proteasome inhibitors, NFκB inhibitors, anti-inflammatory drugs, tissue plasminogen activator (TPA), lipopolysaccharide, UV light, and an intracellular mediator of the TNF-alpha signaling pathway. Such agents induce the apoptosis of autoreactive lymphocytes by interrupting the pathway downstream from TNF-alpha receptor signaling or act downstream of TNF-alpha receptor binding. (Baldwin et al., Ann. Rev. Immunol. (1996) 12:141; Baltimore, Cell (1996) 87:13).

In some embodiments, the anti-FCMR antibodies are used in conjunction with a surgical method of treating or otherwise alleviating autoimmune diseases.

Exemplary therapeutic agents that may be used as part of a combination therapy in treating autoimmune disease, include, for example, In some embodiments, the anti-inflammatory and/or immunosuppressive therapies for combining with the anti-FCMR antibodies include, but are not limited to a TOPK inhibitor (e.g., OTS964 ((R)-9-(4-(1-(dimethylamino)propan-2-yl)phenyl)-8-hydroxy-6-methylthieno[2,3-c]quinolin-4(5H)-one) (Oncotherapy Science)), a tyrosine kinase inhibitor (e.g., axitinib, dasatinib, icotinib), a topoisomerase inhibitor (e.g., topotecan), a sphingosine-1-phosphate receptor agonist (e.g., fingolimod, KRP-203), anti-T cell immunoglobulin (e.g. AtGam), anti-IL-2 receptor antibody (e.g. daclizumab), amides (CTX), ifosfamide (IFO), adriamycin (ADM), daunorubicin (DNR), vincristine (VCR), vinblastine (VBL), etoposide (VP16), vermeer (Vumon), carboplatin (CBP), tacrolimus, sirolimus, everolimus, azathioprine, brequinar, leflunomide, LEA-29Y, anti-CD3 antibody (e.g. OKT3), aspirin, B7-CD28 blocking molecules (e.g. belatacept, abatacept), CD40-CD154 blocking molecules (anti-CD40 antibodies), acetaminophen, ibuprofen, naproxen, piroxicam, and anti-inflammatory steroids (e.g. prednisolone or dexamethasone). Variations of the aforementioned agents that may exhibit differential binding to its cognate receptor, and increased or decreased serum half-life may also be used.

In some embodiments, the anti-inflammatory and/or immunosuppressive therapies for combining with the anti-FCMR antibodies include ablation of autoimmune cells, for example, by administration of TNF-alpha, CFA, interleukin-1 (IL-1), proteasome inhibitors, NFκB inhibitors, anti-inflammatory drugs, tissue plasminogen activator (TPA), lipopolysaccharide, UV light, and an intracellular mediator of the TNF-alpha signaling pathway. Such agents induce the apoptosis of autoreactive lymphocytes by interrupting the pathway downstream from TNF-alpha receptor signaling or act downstream of TNF-alpha receptor binding. (Baldwin et al., Ann. Rev. Immunol. (1996) 12:141; Baltimore, Cell (1996) 87:13).

In some embodiments, the anti-FCMR antibodies are used in conjunction with a surgical method of treating or otherwise alleviating autoimmune diseases.

For example, for treating, delaying the progression of, preventing a relapse of, or alleviating a symptom of multiple sclerosis, the anti-FCMR antibodies that act as FCMR antagonists can be combined with any existing therapy for multiple sclerosis, for example, corticosteroids (e.g., oral prednisone and intravenous methylprednisolone), plasmapheresis, Ocrelizumab, beta interferons, Glatiramer acetate, Dimethyl fumarate, Fingolimod, Feriflunomide, Natalizumab, Alemtuzumab and/or Mitoxantrone.

Exemplary therapeutic agents that may be used as a part of a combination therapy with the anti-FCMR antibodies for treating, delaying the progression of, preventing a relapse of, or alleviating a symptom of a bacterial infection, include, for example, any of a variety of known antibiotic therapeutic agents.

In some embodiments, the antibiotic therapeutic agents in combination with anti-FCMR antibodies for treating bacterial infection include, but are not limited to: β-lactams such as penicillins (e.g., penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, and temocillin), cephalosporins (e.g., cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime), carbapenams (e.g., imipenem, ertapenem, and meropenem), and monobactams (e.g., astreonam); β-lactamase inhibitors (e.g., clavulanate, sulbactam, and tazobactam); aminoglycosides (e.g., streptomycin, neomycin, kanamycin, paromycin, gentamicin, tobramycin, amikacin, netilmicin, spectinomycin, sisomicin, dibekalin, and isepamicin); tetracyclines (e.g., tetracycline, chlortetracycline, demeclocycline, minocycline, oxytetracycline, methacycline, and doxycycline); macrolides (e.g., erythromycin, azithromycin, and clarithromycin); ketolides (e.g., telithromycin); lincosamides (e.g., lincomycin and clindamycin); glycopeptides (e.g., vancomycin, oritavancin, dalbavancin, and teicoplanin); streptogramins (e.g., quinupristin and dalfopristin); sulphonamides (e.g., sulphanilamide, para-aminobenzoic acid, sulfadiazine, sulfisoxazole, sulfamethoxazole, and sulfathalidine); oxazolidinones (e.g., linezolid); quinolones (e.g., nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, and sitafloxacin); metronidazole; daptomycin; garenoxacin; ramoplanin; faropenem; polymyxin; tigecycline; and trimethoprim.

Exemplary therapeutic agents that may be used as a part of a combination therapy with the anti-FCMR antibodies for treating, delaying the progression of, preventing a relapse of, or alleviating a symptom of a viral infection, include, for example, any of a variety of known anti-viral therapeutic agents.

In some embodiments, antiviral therapeutic agents that can be used with the methods of the invention include, but are not limited to, Aciclovir, Acyclovir, Adefovir, Amantadine, Amprenavir, Ampligen, Arbidol, Atazanavir, Atripla, Balavir, Cidofovir, Combivir, Darunavir, Docosanol, Edoxudine, Entecavir, Ecoliever, Famciclovir, Fomivirsen, Foscarnet, Fosfonet, Ganciclovir, Ibacitabine, Imunovir, Idoxuridine, Imiquimod, Inosine, Interferon type III, Interferon type II, Interferon type I, Interferon, Lopinavir, Loviride, Moroxydine, Methisazone, Nexavir, Nitazoxanide, Novir, Peginterferon alfa-2a, Penciclovir, Peramivir, Pleconaril, Podophyllotoxin, Ribavirin, Rimantadine, Pyramidine, Sofosbuvir, Telaprevir, Trifluridine, Trizivir, Tromantadine, Truvada, Valaciclovir, Valganciclovir, Vicriviroc, Vidarabine, Viramidine, Zalcitabine, Zanamivir.

Any drug or combination of drugs disclosed herein may be administered to a subject to treat a disease. The drugs herein can be formulated in any number of ways, often according to various known formulations in the art or as disclosed or referenced herein.

The amount of the antibodies and additional therapeutic agents and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

VI. Pharmaceutical Composition and Administration

The present disclosure also features pharmaceutical compositions/formulations that contain a therapeutically effective amount of an anti-FCMR antibody described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The antibodies of the present disclosure can exist in a lyophilized formulation or liquid aqueous pharmaceutical formulation. The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The antibodies of the present disclosure could exist in a lyophilized formulation including the proteins and a lyoprotectant. The lyoprotectant may be sugar, e.g., disaccharides. In certain embodiments, the lyoprotectant is sucrose or maltose. The lyophilized formulation may also include one or more of a buffering agent, a surfactant, a bulking agent, and/or a preservative.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. It may be administered in the range of 0.1 mg to 1 g and preferably in the range of 0.5 mg to 500 mg of active antibody per administration for adults. Alternatively, a patient's dose can be tailored to the approximate body weight or surface area of the patient.

Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., Clinica Chimica Acta 308: 43-53, 2001; Steimer et al., Clinica Chimica Acta 308: 33-41, 2001).

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

EXAMPLES

The invention now being generally described, will be more readily understood by reference to the following examples, which are included merely for purposes of illustration of certain aspects and embodiments of the present invention, and is not intended to limit the invention.

Example 1—FCMR Surface Expression on Various Hematopoietic Subsets

FCMR surface expression on various hematopoietic subsets in the form of one-dimensional flow cytometry (FCM) representations called histograms. Fresh whole blood from a healthy human donor was stained with the FCMR 2A5 antibody (FIG. 1, left panel) or the FCMR 3F9 antibody (FIG. 1, right panel), as well as antibodies specific for the indicated cell subset. Plots depict FCMR expression by gated CD19+ B cells, CD3+CD4+ T cells or CD3+CD8+ T cells. Mean fluorescence intensity of the FCMR-staining of FCMR+ cells are depicted for each histogram. Fluorescence minus one (FMO) control and an isotype matched antibody were used as controls. FCMR expression is demonstrated on CD19+ B cells, and low FCMR expression is demonstrated on CD4+ or CD8+ T cells. Data are representative of several independent experiments utilizing different human blood samples.

Example 2—the Effect of the FCMR Antibodies or FCMR-Fc Protein on Responsiveness of Lymphocytes in Primary Mixed Lymphocyte Reactions (MLR)

Figure 2:
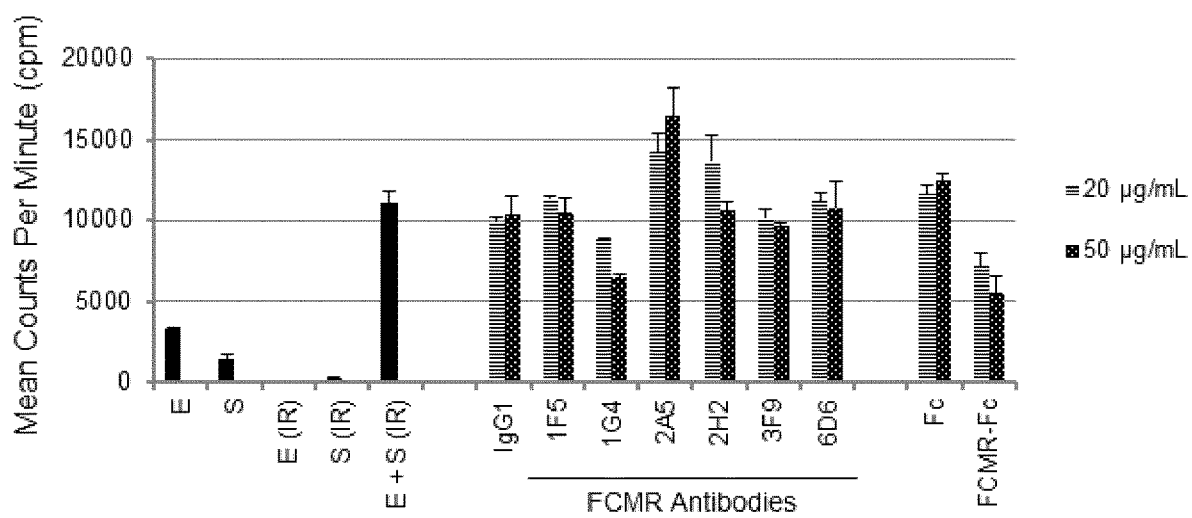
FIG. 2 shows the effect of the FCMR antibodies or FCMR-Fc protein on responsiveness of lymphocytes in primary mixed lymphocyte reactions (MLR).

Peripheral blood mononuclear cells (PBMCs) [$2\times10^5$ cells, effector (E) population] and irradiated (IR) allogenic PBMCs [$1\times10^5$ cells, stimulator (S) population] from healthy human donors were co-cultured in the presence or absence of the indicated amounts of IgG1 isotype control antibody, FCMR antibodies, Fc protein or Fc-FCMR protein. After 4 days, the cells were labeled with 3H-thymidine for an additional 18 hours to measure lymphocyte proliferation. The FCMR 2A5 antibody is shown to stimulate lymphocyte proliferation, and the FCMR 1G4 antibody or FCMR Fc protein is shown to inhibit lymphocyte proliferation (FIG. 2). Data are reported as the mean counts per minute (cpm)±standard error of triplicate wells.

Figure 3:
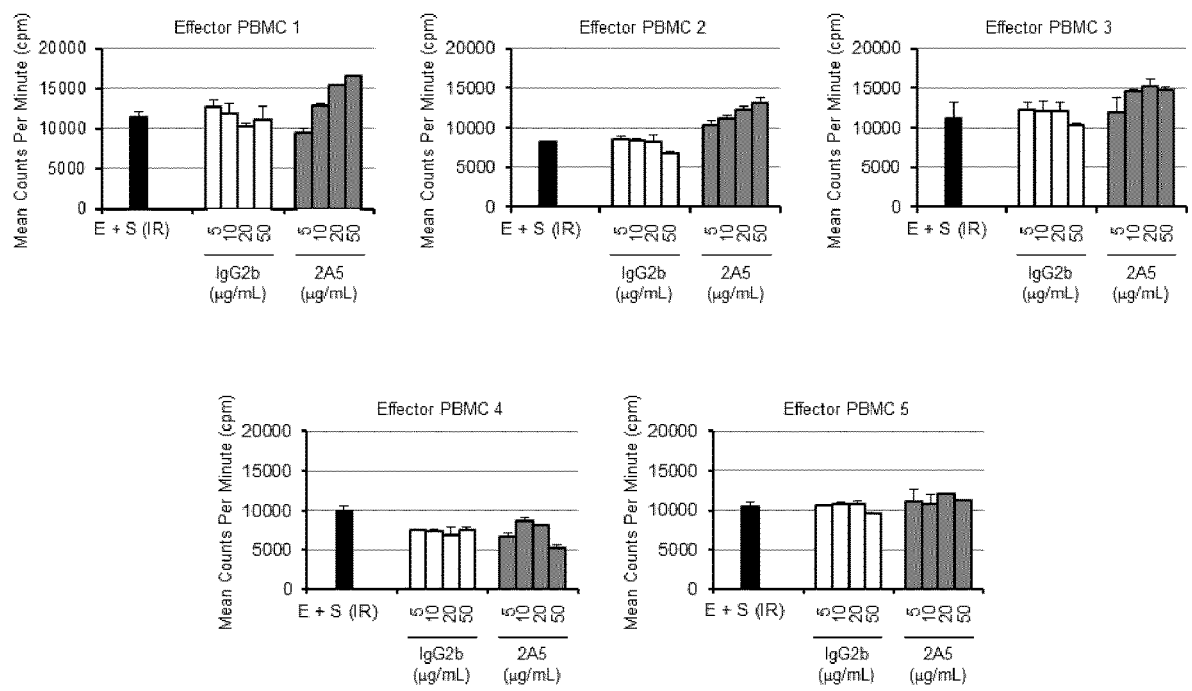
FIG. 3 shows the effect of the FCMR 2A5 antibody on the responsiveness of lymphocytes in primary MLRs.

Example 3—the Effect of the FCMR 2A5 Antibody on Responsiveness of Lymphocytes in Primary MLRs PBMCs [$2\times10^5$ cells, effector (E) population] from five different healthy human donors and irradiated (IR) allogenic PBMCs [$1\times10^5$ cells, stimulator (S) population] from a healthy human donor were co-cultured in the presence or absence of the indicated amounts of IgG2b isotype control antibody or FCMR 2A5 antibody. After 4 days, the cells were labeled with $^3$H-thymidine for an additional 18 hours to measure lymphocyte proliferation. The FCMR 2A5 antibody is shown to stimulate lymphocyte proliferation in three of five effector PBMC samples (FIG. 3). Data are reported as the mean counts per minute (cpm)±standard error of duplicate wells.

Figure 4:
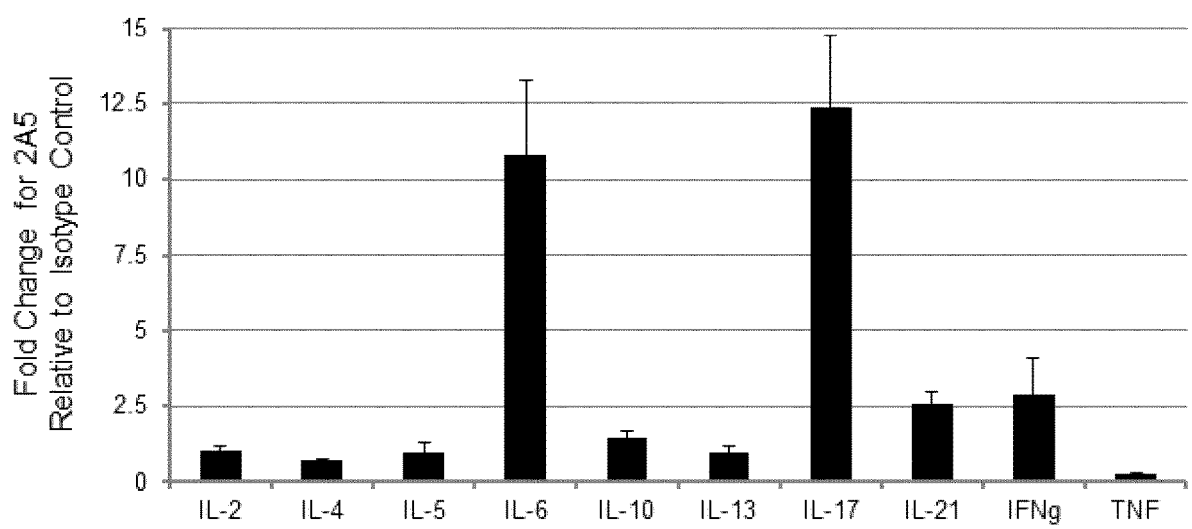
FIG. 4 shows the effect of the FCMR 2A5 antibody on cytokine production by PBMCs in response to a T cell stimulus.

Example 4—the Effect of the FCMR 2A5 Antibody on Cytokine Production by PBMCs in Response to a T Cell Stimulus PBMCs [$2\times10^5$ cells, effector (E) population] from five different healthy human donors and irradiated (IR) allogenic PBMCs [$1\times10^5$ cells, stimulator (S) population] from a healthy human donor were co-cultured in the presence or absence of IgG2b isotype control antibody or FCMR 2A5 antibody (50 µg/mL). After 4.5 days, cytokine levels in culture supernatants were determined by a BioLegend LEGENDplex Human Th Cytokine Panel by manufacturer's instructions. In the presence of 2A5, the level of certain cytokines, including IFNγ, IL-6, IL-17 and IL-21 are increased suggesting that 2A5 causes a skewed Th1-like immune response (FIG. 4). Data are reported as the fold change for [[7C5]]2A5 relative to the isotype control antibody of duplicate wells.

Figure 5:
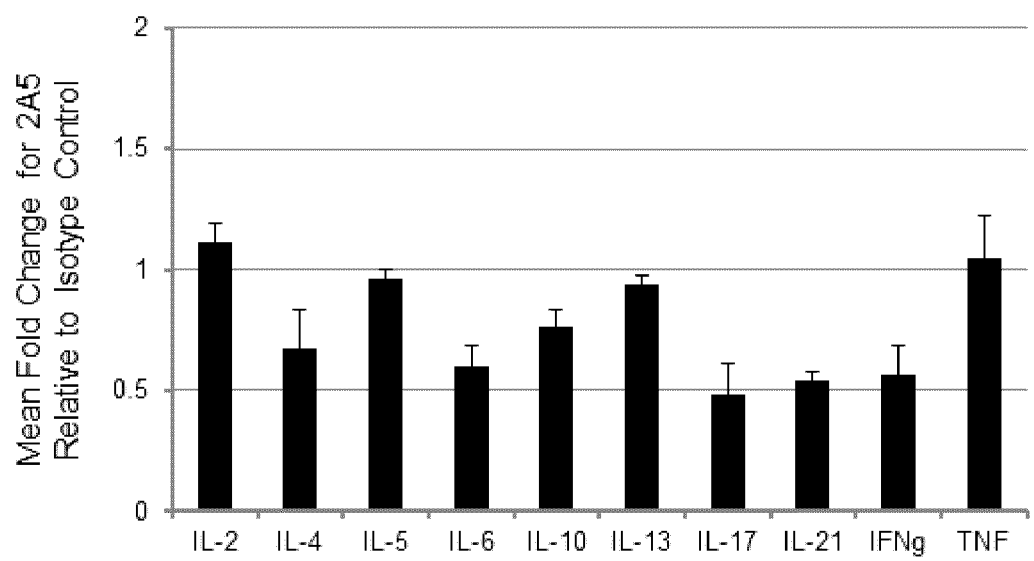
FIG. 5 shows the FCMR 2A5 antibody causes no significant release of cytokines from unstimulated whole blood.

Example 5—the FCMR 2A5 Antibody Causes No Significant Release of Cytokines from Unstimulated Whole Blood Fresh blood from healthy human donors (n=4) was diluted 4:1 with RPMI 1640 medium and cultured for 4 hours in the presence of FCMR 2A5 antibody or IgG2b isotype control antibody (50 µg/mL). LPS (1 µg/mL) was used as a positive control. Cytokine levels in serum samples were determined by a BioLegend LEGENDplex Human Th Cytokine Panel by manufacturer's instructions. The FCMR 2A5 antibody is shown to have no significant stimulatory effect in the absence of a T cell receptor stimulus (FIG. 5). Data are representative of several independent experiments, and are reported as the mean fold change for 2A5 relative to the isotype control antibody of duplicate wells.

Example 6—Affinity of FCMR Antibodies 2A5 and 2H2 for FCMR-Fc Protein Determined by Surface Plasmon Resonance Affinity for FCMR antibodies 2A5 and 2H2 for FCMR-Fc protein was determined by surface plasmon resonance (Biacore) at 25° C. in 10 mM HEPES buffer (pH 7.4), 150 mM NaCl, 3 mM EDTA, 0.05% polysorbate 20 (FIG. 6). Antibodies were immobilized to a target level of 40 RU. Immobilized human IgG was used as a blank surface for reference subtraction. Titration was performed using 500, 250, 125, 62.5, 31.25 and 0 nM FCMR-Fc protein. The equilibrium dissociation constant ($K_D$) was calculated from observed $k_a$ and $k_d$.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An antibody that binds human FCMR, the antibody comprising a heavy chain variable region comprising vhCDR1-3, and a light chain variable region comprising vlCDR1-3, wherein the CDRs are selected from the following:
   a) a vhCDR1 comprising SEQ ID NO:13, a vhCDR2 comprising SEQ ID NO:14, a vhCDR3 comprising SEQ ID NO:15, a vlCDR1 comprising SEQ ID NO:16, a vlCDR2 comprising the amino acid sequence RAN, and a vlCDR3 comprising SEQ ID NO:18;
   b) a vhCDR1 comprising SEQ ID NO:19, a vhCDR2 comprising SEQ ID NO:20, a vhCDR3 comprising SEQ ID NO:21, a vlCDR1 comprising SEQ ID NO:22, a vlCDR2 comprising the amino acid sequence RAN, and a vlCDR3 comprising SEQ ID NO:24;
   c) a vhCDR1 comprising SEQ ID NO:25, a vhCDR2 comprising SEQ ID NO:26, a vhCDR3 comprising SEQ ID NO:27, a vlCDR1 comprising SEQ ID NO:28, a vlCDR2 comprising the amino acid sequence RAN, and a vlCDR3 comprising SEQ ID NO:30;
   d) a vhCDR1 comprising SEQ ID NO:31, a vhCDR2 comprising SEQ ID NO:32, a vhCDR3 comprising SEQ ID NO:33, a vlCDR1 comprising SEQ ID NO:34, a vlCDR2 comprising the amino acid sequence GAS, and a vlCDR3 comprising SEQ ID NO:36;
   e) a vhCDR1 comprising SEQ ID NO:37, a vhCDR2 comprising SEQ ID NO:38, a vhCDR3 comprising SEQ ID NO:39, a vlCDR1 comprising SEQ ID NO:40, a vlCDR2 comprising the amino acid sequence LVS, and a vlCDR3 comprising SEQ ID NO:42; or
   f) a vhCDR1 comprising SEQ ID NO:43, a vhCDR2 comprising SEQ ID NO:44, a vhCDR3 comprising SEQ ID NO:45, a vlCDR1 comprising SEQ ID NO:46, a vlCDR2 comprising the amino acid sequence GAV, and a vlCDR3 comprising SEQ ID NO:48.

2. The antibody according to claim 1, wherein the antibody comprises a constant region with an amino acid sequence at least 90% identical to a human IgG.

3. The antibody according to claim 2, wherein the human IgG is selected from a group consisting of IgG1, IgG2, IgG3 and IgG4.

4. The antibody according to claim 3, wherein the IgG is an IgG2.

5. The antibody according to claim 3, wherein the IgG is an IgG1.

6. A nucleic acid composition encoding the antibody according to claim 1, wherein a first nucleic acid encodes the heavy chain variable region, and wherein a second nucleic acid encodes the light chain variable region.

7. An expression vector composition comprising the nucleic acid composition according to claim 6, wherein the first nucleic acid is contained in a first expression vector and the second nucleic acid is contained in a second expression vector.

8. An expression vector composition comprising the nucleic acid composition according to claim 6, wherein the first nucleic acid and the second nucleic acid are contained in a single expression vector.

9. A host cell comprising the expression vector composition of claim 7.

10. A host cell comprising the expression vector composition of claim 8.

11. A method of making an antibody comprising culturing said host cell of claim 9 under conditions wherein the antibody is expressed, and recovering the antibody.

12. A composition comprising the antibody according to claim 1, and a pharmaceutical acceptable carrier or diluent.

13. A method of modulating an immune response in a subject, the method comprising administering to the subject an effective amount of the antibody according to claim 1 or a nucleic acid composition encoding said antibody.

14. The method of claim 13, wherein the method stimulates an immune response in a subject.

15. The method of claim 13, wherein the method inhibits an immune response in a subject.

16. A method of treating cancer in a subject in need thereof, the method comprising administering to the subject an effective amount of the antibody according to claim 1 or a nucleic acid composition encoding said antibody.

17. The method according to claim 16, wherein the cancer is a B cell malignancy.

18. The method according to claim 16, wherein the cancer is chronic lymphocytic leukemia.

19. The method according to claim 16, wherein the antibody is combined with one or more additional cancer therapeutic agents.

20. The method according to claim 19, wherein the additional cancer therapeutic agents are immune checkpoint inhibitors.

21. The method according to claim 20, wherein the immune checkpoint inhibitors are selected from the group consisting of a PD-1 inhibitor, a PD-L1 inhibitor, a CTLA-4 inhibitor, a TIM-3 inhibitor, and a LAG-3 inhibitor.

22. A method of treating an autoimmune disease in a subject in need thereof, the method comprising administering to the subject an effective amount of the antibody according to claim 1 or a nucleic acid composition encoding said antibody.

23. The method according to claim 22, wherein the antibody is combined with one or more additional anti-inflammatory therapeutic agents.

24. A method of treating a bacterial infection in a subject in need thereof, the method comprising administering to the subject an effective amount of the antibody according to claim 1 or a nucleic acid composition encoding said antibody.

25. The method according to claim 24, wherein the antibody is combined with one or more antibiotic therapeutic agents.

26. A method of treating a viral infection in a subject in need thereof, the method comprising administering to the subject an effective amount of the antibody according to claim 1 or a nucleic acid composition encoding said antibody.

27. The method according to claim 26, wherein the antibody is combined with one or more anti-viral therapeutic agents.

28. A method of modulating FCMR in a subject, the method comprising administering to the subject an effective amount of the antibody according to claim 1 or a nucleic acid composition encoding said antibody.

29. The method of claim 28, wherein modulating FCMR inhibits FCMR activity.

30. The method of claim 28, wherein modulating FCMR promotes FCMR activity.

31. The antibody of claim 1, the antibody comprising a vhCDR1 comprising SEQ ID NO:13, a vhCDR2 comprising SEQ ID NO:14, a vhCDR3 comprising SEQ ID NO:15, a vlCDR1 comprising SEQ ID NO:16, a vlCDR2 comprising the amino acid sequence RAN, and a vlCDR3 comprising SEQ ID NO:18.

32. The antibody that binds human FCMR according to claim 1, the antibody comprising:
   a) a heavy chain variable region comprised in amino acid sequence of SEQ ID NO:1 and a light chain variable region comprised in amino acid sequence of SEQ ID NO:2;
   b) a heavy chain variable region comprised in amino acid sequence of SEQ ID NO:3 and a light chain variable region comprised in amino acid sequence of SEQ ID NO:4;
   c) a heavy chain variable region comprised in amino acid sequence of SEQ ID NO:5 and a light chain variable region comprised in amino acid sequence of SEQ ID NO:6;
   d) a heavy chain variable region comprised in amino acid sequence of SEQ ID NO:7 and a light chain variable region comprised in amino acid sequence of SEQ ID NO:8;
   e) a heavy chain variable region comprised in amino acid sequence of SEQ ID NO:9 and a light chain variable region comprised in amino acid sequence of SEQ ID NO:10; or
   f) a heavy chain variable region comprised in amino acid sequence of SEQ ID NO:11 and a light chain variable region comprised in amino acid sequence of SEQ ID NO:12.

33. The antibody of claim 31, the antibody comprising a heavy chain variable region comprised in amino acid sequence of SEQ ID NO:1 and a light chain variable region comprised in amino acid sequence of SEQ ID NO:2.

* * * * *